(12) United States Patent
Thorson et al.

(10) Patent No.: US 8,278,436 B2
(45) Date of Patent: Oct. 2, 2012

(54) GLYCOSYLATED WARFARIN ANALOGS AND USES THEREOF

(75) Inventors: Jon S. Thorson, Middleton, WI (US); Shannon C. Timmons, Southfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 233 days.

(21) Appl. No.: 12/512,696

(22) Filed: Jul. 30, 2009

(65) Prior Publication Data

US 2010/0267655 A1    Oct. 21, 2010

Related U.S. Application Data

(60) Provisional application No. 61/084,690, filed on Jul. 30, 2008.

(51) Int. Cl.
*C07H 5/06* (2006.01)
*A61K 31/7048* (2006.01)
*G01N 33/52* (2006.01)

(52) U.S. Cl. .............................. 536/29.1; 514/42; 436/94
(58) Field of Classification Search .................. 536/29.1; 514/42; 436/94
See application file for complete search history.

(56) References Cited

PUBLICATIONS

Peltier-Pain et al. ChemMedChem., 2011, 6, p. 1347-1350.*
Zielinska et al. J. Pharmacol. Exp. Ther., 2008, 324, p. 139-148.*
Zacchinga et al. Eur. J. Pharm. Sci., 2004, 23, p. 379-384.*
Ettmayer et al. J. Med. Chem., 2004, 47(10), p. 2393-2404.*
Langenhan et al., "Enhancing the anticancer properties of cardiac glycosides by neoglycorandomization," Proc. Natl. Acad. Sci. U.S.A., 2005, vol. 102, No. 35, pp. 12305-12310.

* cited by examiner

*Primary Examiner* — Shaojia Anna Jiang
*Assistant Examiner* — Jonathan S Lau
(74) *Attorney, Agent, or Firm* — Quarles & Brady LLP

(57) ABSTRACT

The present invention discloses a set of glycosylated warfarin analogs which are useful as anti-tumor or anti-metastatic agents and as reagents for studying sugar uptake in cells.

10 Claims, 31 Drawing Sheets

A

B

A

B

A

B

GLYCOSYLATED WARFARIN ANALOGS AND USES THEREOF

CROSS-REFERENCE TO RELATED APPLICATIONS

This application claims the benefit of U.S. Patent Application No. 61/084,690, filed on Jul. 30, 2008, which is incorporated by reference herein in its entirety.

STATEMENT REGARDING FEDERALLY SPONSORED RESEARCH

This invention was made with United States government support awarded by the National Institutes of Health—Grant Nos. CA84374 and CA 113297. The United States government has certain rights in this invention.

FIELD OF THE INVENTION

This invention relates generally to the synthesis of glycosylated compounds. More particularly, the present invention is directed to glycosylated warfarin analogs and their use as therapeutics and as research tools with novel and/or improved bioactivities.

BACKGROUND OF THE INVENTION

Carbohydrates mediate many essential biological processes. For example, the saccharide-containing macromolecules that decorate cell surfaces are vital to a variety of cellular functions including cell-cell recognition, apoptosis, differentiation, and tumor metastasis. Carbohydrate appendages often play a key role in drug-target interactions. Thus, adding sugar moieties to known compounds can improve the parent compound's pharmacological properties, specificity at multiple levels, or even the molecular mechanism of action, and is a potential strategy for the generation of novel therapeutics. Thorson J S, et al. (2002) in Carbohydrate-Based Drug Discovery, ed. Wong C-H (Wiley-VCH, Weinheim), pp. 685-712; Ahmed A, et al. (2006) J Am Chem Soc 128: 14224-5.

Warfarin, 4-hydroxy-3-(3-oxo-1-phenylbutyl)-2H-1-benzopyran-2-one, is a synthetic analog of the natural anti-coagulant dicumarol. The chemical structure of Warfarin is shown in FIG. 1. This compound has been used extensively as a rodenticide and as an anticoagulant for human use. Glycosylated analogs of warfarin possessing novel and/or improved bioactivities may be useful in developing novel therapeutic compositions and methods of treatment. In addition, warfarin has intrinsic fluorescence, and glycosylated analogs of warfarin compounds could be used as research tools for studying sugar uptake in cells.

SUMMARY OF THE INVENTION

In one embodiment of a first aspect, the invention encompasses a composition comprising one or more of the warfarin neoglycosides having the general formula shown in FIG. 2. The warfarin neoglycosides shown in FIG. 2 are tertiary amines, where one of the three moieties attached to the amino nitrogen is a methoxy moiety, the second of the three moieties attached to the amine nitrogen is a warfarin analog wherein the amino nitrogen substitutes for an oxygen atom in the warfarin molecule, and the third of the three moieties attached to the amino nitrogen is a generalized sugar $(HO)_n$ moiety.

In certain preferred embodiments, the sugar $(HO)_n$ moeity is a reducing sugar selected from an L-sugar, a D-sugar, a deoxy-sugar, a dideoxy-sugar, a glucose epimer, a substituted sugar, a uronic acid, and an oligosaccharide. More preferably, the reducing sugar is selected from the group consisting of L-xylose; D-galactosamine; 2-deoxy-D-galactose; L-rhamnose; D-glucuronic acid; D-lyxose; L-glucose; 2-deoxy-D-glucose; D-xylose; 2-deoxy-L-ribose; 2-deoxy-D-ribose; L-fucose; 2,3,4-tri-O-acetyl-L-rhamnose; D-glucose; L-arabinose; D-mannose; D-galactose; 3-O-methyl-D-glucose; L-mannose; N-acetyl-D-mannosamine; D-arabinose; D-ribose; L-lyxose; N-acetyl-D-galactosamine; L-ribose; D-cellobiose; D-galacturonic acid; D-maltose; D-melibiose; N-acetyl-D-glucosamine; 2,3,4,6-tetra-O-acetyl-D-glucose; maltotriose; D-glucuronic acid lactone; α-lactose; L-sorbose; L-noviose; L-mycarose; D-talose; D-allose; D-fucose; 2,3,4,6-tetra-O-benzyl-D-glucose; 2,3,5-tri-O-benzyl-D-arabinofuranose; N-acetylmuramic acid, D-glucosamine; 2,3,4,6-tetra-O-benzyl-D-mannose; 2,3,5-tri-O-benzyl-D-ribofuranose; L-erythrose; L-gulose; D-digitoxose; 6-deoxy-D-glucose; and 2-deoxy-2-fluoro-D-glucose.

This aspect additionally encompasses compositions comprising the warfarin neoglycosides described above, as well as pharmaceutically acceptable esters, salts, or prodrugs thereof, combined with a pharmaceutically acceptable carrier.

In other embodiments, this aspect encompasses compositions comprising a warfarin neoglycoside produced when an aglycon warfarin analog containing a secondary alkoxylamine moiety is contacted with a reducing sugar selected from the group consisting of a L-sugar, a D-sugar, a deoxy-sugar, a dideoxy-sugar, a glucose epimer, a substituted sugar, a uronic acid, an oligosaccharide and mixtures thereof. Preferably, the reducing sugar is selected from the group consisting of L-xylose; D-galactosamine; 2-deoxy-D-galactose; L-rhamnose; D-glucuronic acid; D-lyxose; L-glucose; 2-deoxy-D-glucose; D-xylose; 2-deoxy-L-ribose; 2-deoxy-D-ribose; L-fucose; 2,3,4-tri-O-acetyl-L-rhamnose, D-glucose; L-arabinose; D-mannose; D-galactose; 3-O-methyl-D-glucose; L-mannose; N-acetyl-D-mannosamine; D-arabinose; D-ribose; L-lyxose; N-acetyl-D-galactosamine; L-ribose; D-cellobiose; D-galacturonic acid; D-maltose; D-melibiose; N-acetyl-D-glucosamine; 2,3,4,6-tetra-O-acetyl-D-glucose; maltotriose; D-glucuronic acid lactone; α-lactose; L-sorbose; L-noviose; L-mycarose; D-talose; D-allose; D-fucose; 2,3,4,6-tetra-O-benzyl-D-glucose; 2,3,5-tri-O-benzyl-D-arabinofuranose; N-acetylmuramic acid, D-glucosamine; 2,3,4,6-tetra-O-benzyl-D-mannose; 2,3,5-tri-O-benzyl-D-ribofuranose; L-erythrose; L-gulose; D-digitoxose; 6-deoxy-D-glucose; 2-deoxy-2-fluoro-D-glucose; and mixtures thereof. Preferably, the aglycon warfarin analog is the compound having the formula shown in FIG. 4.

This aspect additionally encompasses compositions comprising the warfarin neoglycosides described above, as well as pharmaceutically acceptable esters, salts, or prodrugs thereof, combined with a pharmaceutically acceptable carrier.

In a second aspect, the invention encompasses methods of treating a subject having cancer cells. The methods comprise the step of contacting the cancer cells with an effective amount of one or more of a warfarin neoglyoside having the general formula shown in FIG. 2. Preferably, the sugar $(HO)_n$ moiety attached to the nitrogen atom in the warfarin neoglycoside is selected from the group consisting of L-xylose; D-galactosamine; 2-deoxy-D-galactose; L-rhamnose; D-glucuronic acid; D-lyxose; L-glucose; 2-deoxy-D-glucose;

D-xylose; 2-deoxy-L-ribose; 2-deoxy-D-ribose; L-fucose; 2,3,4-tri-O-acetyl-L-rhamnose; D-glucose; L-arabinose; D-mannose; D-galactose; 3-O-methyl-D-glucose; L-mannose; N-acetyl-D-mannosamine; D-arabinose; D-ribose; L-lyxose; N-acetyl-D-galactosamine; L-ribose; D-cellobiose; D-galacturonic acid; D-maltose; D-melibiose; N-acetyl-D-glucosamine; 2,3,4,6-tetra-O-acetyl-D-glucose; maltotriose; D-glucuronic acid lactone; α-lactose; L-sorbose; L-noviose; L-mycarose; D-talose; D-allose; D-fucose; 2,3,4,6-tetra-O-benzyl-D-glucose; 2,3,5-tri-O-benzyl-D-arabinofuranose; N-acetylmuramic acid, D-glucosamine; 2,3,4,6-tetra-O-benzyl-D-mannose; 2,3,5-tri-O-benzyl-D-ribofuranose; L-erythrose; L-gulose; D-digitoxose; 6-deoxy-D-glucose; and 2-deoxy-2-fluoro-D-glucose. More preferably, the sugar $(HO)_n$ moiety is selected from the group consisting of L-xylose; D-lyxose; D-xylose; 2-deoxy-L-ribose; 2-deoxy-D-ribose; L-fucose; L-arabinose; D-ribose; L-lyxose; L-ribose; 2,3,4,6-tetra-O-acetyl-D-glucose; L-mycarose; 2,3,4,6-tetra-O-benzyl-D-glucose; 2,3,5-tri-O-benzyl-D-arabinofuranose; 2,3,4,6-tetra-O-benzyl-D-mannose; 2,3,5-tri-O-benzyl-D-ribofuranose; 6-deoxy-D-glucose; and 2-deoxy-2-fluoro-D-glucose. Most preferably, the sugar $(HO)_n$ moiety is selected from the group consisting of L-xylose; D-lyxose; D-xylose; 2-deoxy-L-ribose; 2-deoxy-D-ribose; L-fucose; L-lyxose; 2,3,4,6-tetra-O-acetyl-D-glucose; L-mycarose; 2,3,5-tri-O-benzyl-D-arabinofuranose; 2,3,4,6-tetra-O-benzyl-D-mannose; 2,3,5-tri-O-benzyl-D-ribofuranose; 6-deoxy-D-glucose; and 2-deoxy-2-fluoro-D-glucose.

In certain embodiments, a pharmaceutically acceptable ester, salt or prodrug of the described warfarin neoglycosides is used in the described method of treatment.

In certain preferred embodiments, the cancer cells being contacted with an effective amount of the warfarin neoglycoside or pharmaceutically acceptable ester, salt or prodrug thereof are selected from human lung adenocarcinoma cells, human colorectal adenocarcinoma cells, human ovarian adenocarcinoma cells, human central nervous system adenocarcinoma cells, and human breast adenocarcinoma cells; more preferably, the cancer cells being contacted are human colorectal adenocarcinoma cells.

In a third aspect, the invention encompasses a method of studying sugar uptake in cells. The method includes the step of contacting cells with a warfarin neoglyoside having the general formula set forth in FIG. 2. Preferably, the sugar $(HO)_n$ moiety attached to the nitrogen atom in the neoglycosides is selected from the group consisting of L-xylose; D-galactosamine; 2-deoxy-D-galactose; L-rhamnose; D-glucuronic acid; D-lyxose; L-glucose; 2-deoxy-D-glucose; D-xylose; 2-deoxy-L-ribose; 2-deoxy-D-ribose; L-fucose; 2,3,4-tri-O-acetyl-L-rhamnose; D-glucose; L-arabinose; D-mannose; D-galactose; 3-O-methyl-D-glucose; L-mannose; N-acetyl-D-mannosamine; D-arabinose; D-ribose; L-lyxose; N-acetyl-D-galactosamine; L-ribose; D-cellobiose; D-galacturonic acid; D-maltose; D-melibiose; N-acetyl-D-glucosamine; 2,3,4,6-tetra-O-acetyl-D-glucose; maltotriose; D-glucuronic acid lactone; α-lactose; L-sorbose; L-noviose; L-mycarose; D-talose; D-allose; D-fucose; 2,3,4,6-tetra-O-benzyl-D-glucose; 2,3,5-tri-O-benzyl-D-arabinofuranose; N-acetylmuramic acid, D-glucosamine; 2,3,4,6-tetra-O-benzyl-D-mannose; 2,3,5-tri-O-benzyl-D-ribofuranose; L-erythrose; L-gulose; D-digitoxose; 6-deoxy-D-glucose; and 2-deoxy-2-fluoro-D-glucose.

This aspect also includes the step of measuring the amount of the warfarin neoglycoside taken up by the cells. In certain preferred embodiments of the method, this step is performed by a fluorescence-based assay.

Other objects, features and advantages of the present invention will become apparent after review of the specification, claims and drawings.

BRIEF DESCRIPTION OF THE DRAWINGS

FIG. 7A is a trace for the neoglycoside wherein the sugar $(OH)_n$ moiety is 1-xylose, and FIG. 7B is a trace for the neoglycoside wherein the sugar $(OH)_n$ moiety is 2-deoxy-D-galactose.

FIG. 8A is a trace for the neoglycoside wherein the sugar $(OH)_n$ moiety is L-rhamnose, and FIG. 8B is a trace for the neoglycoside wherein the sugar $(OH)_n$ moiety is D-glucuronic acid.

FIG. 9A is a trace for the neoglycoside wherein the sugar $(OH)_n$ moiety is D-lyxose, and FIG. 9B is a trace for the neoglycoside wherein the sugar $(OH)_n$ moiety is L-glucose.

FIG. 10A is a trace for the neoglycoside wherein the sugar $(OH)_n$ moiety is 2-deoxy-D-glucose, and FIG. 10B is a trace for the neoglycoside wherein the sugar $(OH)_n$ moiety is D-xylose.

FIG. 11A is a trace for the neoglycoside wherein the sugar $(OH)_n$ moiety is 2-deoxy-L-ribose, and FIG. 11B is a trace for the neoglycoside wherein the sugar $(OH)_n$ moiety is 2-deoxy-D-ribose.

FIG. 12A is a trace for the neoglycoside wherein the sugar $(OH)_n$ moiety is L-fucose, and FIG. 12B is a trace for the neoglycoside wherein the sugar $(OH)_n$ moiety is D-glucose.

FIG. 13A is a trace for the neoglycoside wherein the sugar $(OH)_n$ moiety is L-arabinose, and FIG. 13B is a trace for the neoglycoside wherein the sugar $(OH)_n$ moiety is D-mannose.

FIG. 14A is a trace for the neoglycoside wherein the sugar $(OH)_n$ moiety is D-galactose, and FIG. 14B is a trace for the neoglycoside wherein the sugar $(OH)_n$ moiety is 3-O-methyl-D-glucose.

FIG. 15A is a trace for the neoglycoside wherein the sugar $(OH)_n$ moiety is L-mannose, and FIG. 15B is a trace for the neoglycoside wherein the sugar $(OH)_n$ moiety is N-acetyl-D-mannosamine.

FIG. 16A is a trace for the neoglycoside wherein the sugar $(OH)_n$ moiety is D-arabinose, and FIG. 16B is a trace for the neoglycoside wherein the sugar $(OH)_n$ moiety is D-ribose.

FIG. 17A is a trace for the neoglycoside wherein the sugar $(OH)_n$ moiety is L-lyxose, and FIG. 17B is a trace for the neoglycoside wherein the sugar $(OH)_n$ moiety is N-acetyl-D-galctosamine.

FIG. 18A is a trace for the neoglycoside wherein the sugar $(OH)_n$ moiety is L-ribose, and FIG. 18B is a trace for the neoglycoside wherein the sugar $(OH)_n$ moiety is D-galacturonic acid.

FIG. 19A is a trace for the neoglycoside wherein the sugar $(OH)_n$ moiety is D-maltose, and FIG. 19B is a trace for the neoglycoside wherein the sugar $(OH)_n$ moiety is D-melibiose.

FIG. 20A is a trace for the neoglycoside wherein the sugar $(OH)_n$ moiety is N-acetyl-D-glucosamine, and FIG. 20B is a trace for the neoglycoside wherein the sugar $(OH)_n$ moiety is maltotriose.

FIG. 21A is a trace for the neoglycoside wherein the sugar $(OH)_n$ moiety is D-glucuronic acid γ-lactone, and FIG. 21B is a trace for the neoglycoside wherein the sugar $(OH)_n$ moiety is L-noviose.

FIG. 22A is a trace for the neoglycoside wherein the sugar $(OH)_n$ moiety is L-mycarose, and FIG. 22B is a trace for the neoglycoside wherein the sugar $(OH)_n$ moiety is D-talose.

FIG. 23A is a trace for the neoglycoside wherein the sugar $(OH)_n$ moiety is D-allose, and FIG. 23B is a trace for the neoglycoside wherein the sugar $(OF)_n$ moiety is L-fucose.

FIG. 24A is a trace for the neoglycoside wherein the sugar $(OH)_n$ moiety is L-erythrose, and FIG. 24B is a trace for the neoglycoside wherein the sugar $(OH)_n$ moiety is L-gulose.

FIG. 25A is a trace for the neoglycoside wherein the sugar $(OH)_n$ moiety is D-digitoxose, and FIG. 25B is a trace for the neoglycoside wherein the sugar $(OH)_n$ moiety is 6-deoxy-D-glucose.

DETAILED DESCRIPTION OF THE INVENTION

1. Definitions

Figure 1:
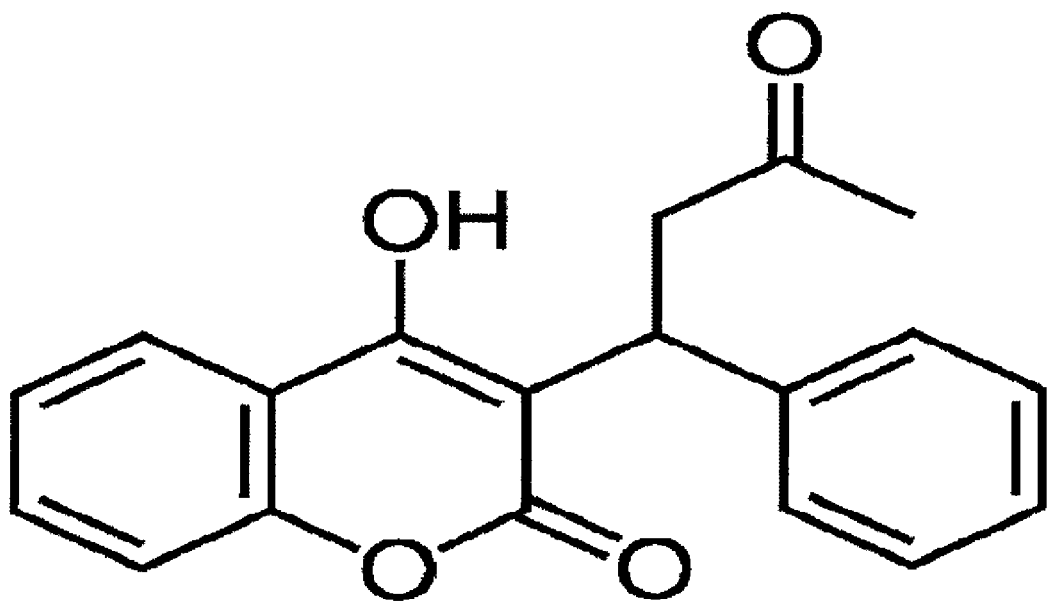
FIG. 1 shows the chemical structure of warfarin, 4-hydroxy-3-(3-oxo-1-phenylbutyl)-2H-1-benzopyran-2-one.

It must be noted that as used herein and in the appended claims, the singular forms "a", "an", and "the" include the plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

"Subject" means mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable carrier" as used herein means a chemical composition with which a biologically active ingredient can be combined and which, following the combination, can be used to administer the active ingredient to a subject.

A "pharmaceutically acceptable" ester or salt as used herein means an ester or salt form of the active ingredient which is compatible with any other ingredients of the pharmaceutical composition and which is not deleterious to the subject to which the composition is to be administered. The terms "pharmaceutically acceptable salts" or "prodrugs" includes the salts and prodrugs of compounds that are, within the scope of sound medical judgment, suitable for use with patients without undue toxicity, irritation, allergic response, and the like, commensurate with a reasonable benefit/risk ratio, and effective for their intended use, as well as the zwitterionic forms, where possible, of the compounds.

"Pro-drug" means a pharmacologically inactive form of a compound which must be metabolized in vivo by a subject after administration into a pharmacologically active form of the compound in order to produce the desired pharmacological effect. After administration to the subject, the pharmacologically inactive form of the compound is converted in vivo under the influence of biological fluids or enzymes into a pharmacologically active form of the compound. Although metabolism occurs for many compounds primarily in the liver, almost all other tissues and organs, especially the lung, are able to carry out varying degrees of metabolism. For example, metabolism of the pro-drug may take place by hydrolysis in blood. Pro-drug forms of compounds may be utilized, for example, to improve bioavailability, mask unpleasant characteristics such as bitter taste, alter solubility for intravenous use, or to provide site-specific delivery of the compound. Reference to a compound herein includes pro-drug forms of a compound.

A discussion of the use of pro-drugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987. For example, if a compound Contains a carboxylic acid functional group, a pro-drug can comprise an ester formed by the replacement of the hydrogen atom of the acid group with a group such as $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

Similarly, if a compound comprises an alcohol functional group, a pro-drug can be formed by the replacement of the hydrogen atom of the alcohol group with a group such as $(C_1-C_6)$alkanoyloxymethyl, 1-$(C_1-C_6)$alkanoyloxy)ethyl, 1-methyl-1-$(C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanoyl, arylacyl and alpha-aminoacyl, or alpha-aminoacyl-alpha-aminoacyl, where each alpha-aminoacyl group is independently selected from the naturally occurring L-amino acids, P(O)(OH)$_2$, —P(O)(O$(C_1-C_6)$alkyl)$_2$ or glycosyl (the radical resulting from the removal of a hydroxyl group of the hemiacetal form of a carbohydrate).

If a compound comprises an amine functional group, a pro-drug can be formed by the replacement of a hydrogen atom in the amine group with a group such as R-carbonyl, RO-carbonyl, NRR'-carbonyl where R and R' are each independently $(C_1-C_{10})$alkyl, $(C_3-C_7)$cycloalkyl, benzyl, or R-carbonyl is a natural alpha-aminoacyl or natural alpha-aminoacyl-, —C(OH)C(O)OY wherein Y is H, $(C_1-C_6)$alkyl or benzyl, —C(OY$_0$)Y$_1$ wherein Y$_0$ is $(C_1-C_4)$ alkyl and Y$_1$ is ($(C_1-C_6)$alkyl, carboxy$(C_1-C_6)$alkyl, amino$(C_1-C_4)$alkyl or mono-N- or di-N,N—$(C_1-C_6)$alkylaminoalkyl, —C(Y$_2$)Y$_3$ wherein Y$_2$ is H or methyl and Y$_3$ is mono-N- or di-N,N—$(C_1-C_6)$-alkylamino, morpholino, piperidin-1-yl or pyrrolidin-1-yl.

The term "salts" refers to inorganic and organic salts of compounds. These salts can be prepared in situ during the final isolation and purification of a compound, or by separately reacting a purified compound with a suitable organic or inorganic acid or base, as appropriate, and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, besylate, esylate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Compounds having N-oxides of amino groups, such as produced by reaction with hydrogen peroxide, are also encompassed.

A "therapeutically effective amount" means an amount of a compound that, when administered to a subject for treating a disease, is sufficient to effect such treatment for the disease.

The "therapeutically effective amount" will vary depending on the compound, the disease state being treated, the severity or the disease treated, the age and relative health of the subject, the route and form of administration, the judgment of the attending medical or veterinary practitioner, and other factors.

For purposes of the present invention, "treating" or "treatment" describes the management and care of a patient for the purpose of combating the disease, condition, or disorder. The terms embrace both preventative, i.e., prophylactic, and palliative treatment. Treating includes the administration of a compound of present invention to prevent the onset of the symptoms or complications, alleviating the symptoms or complications, or eliminating the disease, condition, or disorder.

2. The Invention

The inventors have used a three step glycorandomization procedure to synthesize a number of novel warfarin neoglycosides. Further, the inventors have demonstrated the biological activity of selected novel warfarin neoglycosides against certain tumor cell lines. Given the intrinsic fluorescent properties of warfarin, the warfarin neoglycosides of the present invention may also be used as research tools for studying sugar uptake in cells.

Accordingly, the invention provides in a first aspect a composition comprising one or more of the newly synthesized glycolsylated analogs of warfarin. These warfarin neoglycosides have the general chemical formula shown in FIG. 2. Note that in the general chemical formula, the aglycon moiety is specified as a warfarin oxyamino analog attached through the amino nitrogen to a general sugar moiety ring with a varying number of alcohol groups attached (designated as $(HO)_n$). Although all of the warfarin neoglycosides of the present invention contain the same methoxyamino warfarin analog moiety, they differ in the specific sugar moiety attached to this aglycon.

In preferred embodiments, the sugar $(HO)_n$ attached to the nitrogen atom is a reducing sugar selected from the group consisting of an L-sugar, a D-sugar, a deoxy-sugar, a dideoxy-sugar, a glucose epimer, a substituted sugar, a uronic acid, and an oligosaccharide. In more preferred embodiments, the reducing sugar is selected from the group consisting of L-xylose; D-galactosamine; 2-deoxy-D-galactose; L-rhamnose; D-glucuronic acid; D-lyxose; L-glucose; 2-deoxy-D-glucose; D-xylose; 2-deoxy-L-ribose; 2-deoxy-D-ribose; L-fucose; 2,3,4-tri-O-acetyl-L-rhamnose; D-glucose; L-arabinose; D-mannose; D-galactose; 3-O-methyl-D-glucose; L-mannose; N-acetyl-D-mannosamine; D-arabinose; D-ribose; L-lyxose; N-acetyl-D-galactosamine; L-ribose; D-cellobiose; D-galacturonic acid; D-maltose; D-melibiose; N-acetyl-D-glucosamine; 2,3,4,6-tetra-O-acetyl-D-glucose; maltotriose; D-glucuronic acid lactone; α-lactose; L-sorbose; L-noviose; L-mycarose; D-talose; D-allose; D-fucose; 2,3,4,6-tetra-O-benzyl-D-glucose; 2,3,5-tri-O-benzyl-D-arabinofuranose; N-acetylmuramic acid, D-glucosamine; 2,3,4,6-tetra-O-benzyl-D-mannose; 2,3,5-tri-O-benzyl-D-ribofuranose; L-erythrose; L-gulose; D-digitoxose; 6-deoxy-D-glucose; and 2-deoxy-2-fluoro-D-glucose.

Figure 3:
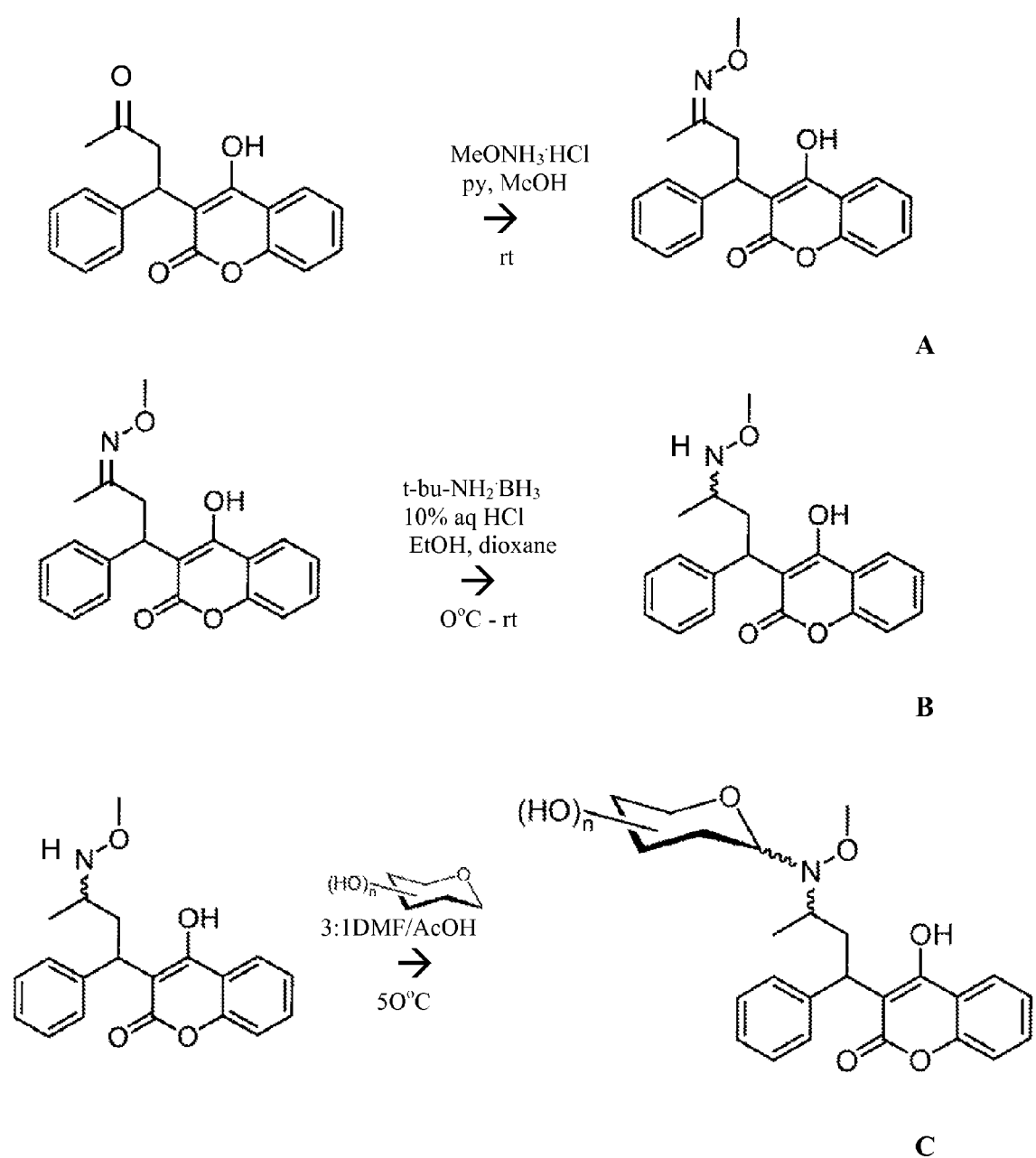
FIG. 3 is a schematic drawing showing the three steps of the general chemical synthesis strategy used to synthesize the warfarin neoglycosides of the present invention, using warfarin as the initial starting compound.

As outlined in more detail in the Example section below, the inventors synthesized the warfarin neoglycosides of the present invention through the three step process illustrated in FIG. 3. In the first step (FIG. 3A), warfarin is reacted to produce warfarin oxime. In the second step (FIG. 3B), warfarin oxime is further reacted to produce the methoxyamino warfarin aglygon shown in FIG. 4. Finally, the warfarin aglygon is contacted with the desired sugar to produce the warfarin neoglycoside having that particular sugar moiety (FIG. 3C).

Accordingly, the invention encompasses compositions comprising warfarin neoglycosides produced by contacting an aglycon warfarin analog having a secondary alkoxylamine moiety with a reducing sugar selected from the group consisting of a L-sugar, a D-sugar, a deoxy-sugar, a dideoxy-sugar, a glucose epimer, a substituted sugar, a uronic acid, an oligosaccharide, and mixtures thereof. In certain embodiments, the aglycon warfarin analog contacting the reducing sugar is the compound having the chemical structure shown in FIG. 4, and the reducing sugar is selected from the group consisting of L-xylose; D-galactosamine; 2-deoxy-D-galactose; L-rhamnose; D-glucuronic acid; D-lyxose; L-glucose; 2-deoxy-D-glucose; D-xylose; 2-deoxy-L-ribose; 2-deoxy-D-ribose; L-fucose; 2,3,4-tri-O-acetyl-L-rhamnose; D-glucose; L-arabinose; D-mannose; D-galactose; 3-O-methyl-D-glucose; L-mannose; N-acetyl-D-mannosamine; D-arabinose; D-ribose; L-lyxose; N-acetyl-D-galactosamine; L-ribose; D-cellobiose; D-galacturonic acid; D-maltose; D-melibiose; N-acetyl-D-glucosamine; 2,3,4,6-tetra-O-acetyl-D-glucose; maltotriose; D-glucuronic acid lactone; α-lactose; L-sorbose; L-noviose; L-mycarose; D-talose; D-allose; D-fucose; 2,3,4,6-tetra-O-benzyl-D-glucose; 2,3,5-tri-O-benzyl-D-arabinofuranose; N-acetylmuramic acid, D-glucosamine; 2,3,4,6-tetra-O-benzyl-D-mannose; 2,3,5-tri-O-benzyl-D-ribofuranose; L-erythrose; L-gulose; D-digitoxose; and 6-deoxy-D-glucose; and 2-deoxy-2-fluoro-D-glucose.

As further shown in the Example section below, the inventors have demonstrated that some of the compositions of the present invention exhibit biological activity against certain tumor cell lines. Thus, in a second aspect, the invention encompasses a method of treating a subject having cancer cells by contacting the cancer cells with an effective amount of one or more of the warfarin neoglyosides described above, a pharmaceutically acceptable ester, salt, or prodrugs thereof. Accordingly, in certain embodiments, the compositions of the present invention may encompass pharmaceutically acceptable esters, salts, or prodrugs of the warfarin neoglocosides described above. In some preferred embodiments, the compositions of the present invention may include a pharmaceutically acceptable carrier.

In some preferred embodiments of the method of treating a subject having cancer cells, the cancer cells being contacted with an effective amount of one or more of the warfarin neoglycosides, pharmaceutically acceptable esters, salts, or prodrugs thereof are selected from human lung adenocarcinoma cells, human colorectal adenocarcinoma cells, human ovarian adenocarcinoma cells, human central nervous system adenocarcinoma cells, and human breast adenocarcinoma cells. Most preferably, the cancer cells being contacted are human colorectal adenocarcinoma cells.

In preferred embodiments of the method, the sugar $(HO)_n$ attached to the nitrogen atom in the warfarin neoglyoside used in the method is selected from the group consisting of L-xylose; D-lyxose; D-xylose; 2-deoxy-L-ribose; 2-deoxy-D-ribose; L-fucose; L-arabinose; D-ribose; L-lyxose; L-ribose; 2,3,4,6-tetra-O-acetyl-D-glucose; L-mycarose; 2,3,4, 6-tetra-O-benzyl-D-glucose; 2,3,5-tri-O-benzyl-D-arabinofuranose; 2,3,4,6-tetra-O-benzyl-D-mannose; 2,3,5-tri-O-benzyl-D-ribofuranose; 6-deoxy-D-glucose; and 2-deoxy-2-fluoro-D-glucose. More preferably, the sugar $(HO)_n$ attached to the nitrogen atom in the warfarin neoglyoside used in the method is selected from the group consisting of L-xylose; D-lyxose; D-xylose; 2-deoxy-L-ribose;

2-deoxy-D-ribose; L-fucose; L-lyxose; 2,3,4,6-tetra-O-acetyl-D-glucose; L-mycarose; 2,3,5-tri-O-benzyl-D-arabinofuranose; 2,3,4,6-tetra-O-benzyl-D-mannose; 2,3,5-tri-O-benzyl-D-ribofuranose; 6-deoxy-D-glucose; and 2-deoxy-2-fluoro-D-glucose.

The form in which the active compound is administered to the cells is not critical; the active compound need only reach the cells, directly or indirectly. The invention encompasses preparation and use of medicaments and pharmaceutical compositions comprising a compound described herein as an active ingredient.

A warfarin neoglycoside is administered to a patient in a therapeutically effective amount. A warfarin neoglycoside can be administered alone or as part of a pharmaceutically acceptable composition. In addition, a compound or composition can be administered all at once, as for example, by a bolus injection, multiple times, such as by a series of tablets, or delivered substantially uniformly over a period of time, as for example, using transdermal delivery. It is also noted that the dose of the compound can be varied over time. A warfarin neoglycoside can be administered using an immediate release formulation, a controlled release formulation, or combinations thereof. The term "controlled release" includes sustained release, delayed release, and combinations thereof.

A pharmaceutical composition of the invention can be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a patient or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the human treated and further depending upon the route by which the composition is to be administered. By way of example, the composition can comprise between 0.1% and 100% (w/w) active ingredient. A unit dose of a pharmaceutical composition of the invention will generally comprise from about 100 milligrams to about 2 grams of the active ingredient, and preferably comprises from about 200 milligrams to about 1.0 gram of the active ingredient.

In addition, a warfarin neoglycoside can be administered alone, in combination with other warfarin neoglycosides, or with other pharmaceutically active compounds. The other pharmaceutically active compounds can be selected to treat the same disease as the warfarin neoglycoside or a different disease. If the patient is to receive or is receiving multiple pharmaceutically active compounds, the compounds can be administered simultaneously or sequentially in any order. For example, in the case of tablets, the active compounds may be found in one tablet or in separate tablets, which can be administered at once or sequentially in any order. In addition, it should be recognized that the compositions can be different forms. For example, one or more compounds may be delivered via a tablet, while another is administered via injection or orally as a syrup.

Another aspect of the invention relates to a kit comprising a pharmaceutical composition of the invention and instructional material. Instructional material includes a publication, a recording, a diagram, or any other medium of expression which is used to communicate the usefulness of the pharmaceutical composition of the invention for one of the purposes set forth herein in a human. The instructional material can also, for example, describe an appropriate dose of the pharmaceutical composition of the invention. The instructional material of the kit of the invention can, for example, be affixed to a container which contains a pharmaceutical composition of the invention or be shipped together with a container which contains the pharmaceutical composition. Alternatively, the instructional material can be shipped separately from the container with the intention that the instructional material and the pharmaceutical composition be used cooperatively by the recipient.

The invention also includes a kit comprising a pharmaceutical composition of the invention and a delivery device for delivering the composition to a human. By way of example, the delivery device can be a squeezable spray bottle, a metered-dose spray bottle, an aerosol spray device, an atomizer, a dry powder delivery device, a self-propelling solvent/powder-dispensing device, a syringe, a needle, a tampon, or a dosage-measuring container. The kit can further comprise an instructional material as described herein. For example, a kit may comprise two separate pharmaceutical compositions comprising respectively a first composition comprising a warfarin neoglycoside and a pharmaceutically acceptable carrier; and a composition comprising second pharmaceutically active compound and a pharmaceutically acceptable carrier. The kit also comprises a container for the separate compositions, such as a divided bottle or a divided foil packet. Additional examples of containers include syringes, boxes, bags, and the like. Typically, a kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of a kit is a blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and a sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen that the tablets or capsules so specified should be ingested. Another example of such a memory aid is a calendar printed on the card, e.g., as follows "First Week, Monday, Tuesday, . . . etc. . . . Second Week, Monday, Tuesday," etc. Other variations of memory aids will be readily apparent. A "daily dose" can be a single tablet or capsule or several pills or capsules to be taken on a given day. Also, a daily dose of a warfarin neoglycoside composition can consist of one tablet or capsule, while a daily dose of the second compound can consist of several tablets or capsules and vice versa. The memory aid should reflect this and assist in correct administration.

In another embodiment of the present invention, a dispenser designed to dispense the daily doses one at a time in the order of their intended use is provided. Preferably, the dispenser is equipped with a memory aid, so as to further facilitate compliance with the dosage regimen. An example of such a memory aid is a mechanical counter, which indicates the number of daily doses that have been dispensed. Another example of such a memory aid is a battery-powered microchip memory coupled with a liquid crystal readout, or audible reminder signal which, for example, reads out the date that the last daily dose has been taken and/or reminds one when the next dose is to be taken.

In the treatment method of the present invention, a warfarin neoglycoside composition, optionally comprising other pharmaceutically active compounds, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. Other contemplated formulations include projected nanoparticles, liposomal preparations, resealed erythrocytes containing the active ingredient, and immunologically-based formulations.

Parenteral administration of a pharmaceutical composition includes any route of administration characterized by physical breaching of a tissue of a human and administration of the pharmaceutical composition through the breach in the tissue. Parenteral administration thus includes administration of a pharmaceutical composition by injection of the composition, by application of the composition through a surgical, incision, by application of the composition through a tissue-penetrating non-surgical wound, and the like. In particular, parenteral administration includes subcutaneous, intraperitoneal, intravenous, intraarterial, intramuscular, or intrasternal injection and intravenous, intraarterial, or kidney dialytic infusion techniques.

Compositions suitable for parenteral injection comprise the active ingredient combined with a pharmaceutically acceptable carrier such as physiologically acceptable sterile aqueous or nonaqueous solutions, dispersions, suspensions, or emulsions, or may comprise sterile powders for reconstitution into sterile injectable solutions or dispersions. Examples of suitable aqueous and nonaqueous carriers, diluents, solvents, or vehicles include water, isotonic saline, ethanol, polyols (propylene glycol, polyethylene glycol, glycerol, and the like), suitable mixtures thereof, triglyceride, including vegetable oils such as olive oil, or injectable organic esters such as ethyl oleate. Proper fluidity can be maintained, for example, by the use of a coating such as lecithin, by the maintenance of the required particle size in the case of dispersions, and/or by the use of surfactants. Such formulations can be prepared, packaged, or sold in a form suitable for bolus administration or for continuous administration. Injectable formulations can be prepared, packaged, or sold in unit dosage form, such as in ampules, in multi-dose containers containing a preservative, or in single-use devices for auto-injection or injection by a medical practitioner.

Formulations for parenteral administration include suspensions, solutions, emulsions in oily or aqueous vehicles, pastes, and implantable sustained-release or biodegradable formulations. Such formulations can further comprise one or more additional ingredients including suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions can be prepared, packaged, or sold in the form of a sterile injectable aqueous or oily suspension or solution. This suspension or solution can be formulated according to the known art, and can comprise, in addition to the active ingredient, additional ingredients such as the dispersing agents, wetting agents, or suspending agents described herein. Such sterile injectable formulations can be prepared using a non-toxic parenterally-acceptable diluent or solvent, such as water or 1,3-butanediol, for example. Other acceptable diluents and solvents include Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation can comprise pharmaceutically acceptable polymeric or hydrophobic materials such as an emulsion, an ion exchange resin, a sparingly soluble polymer, or a sparingly soluble salt.

These compositions may also contain adjuvants such as preserving, wetting, emulsifying, and/or dispersing agents. Prevention of microorganism contamination of the compositions can be accomplished by the addition of various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and/or gelatin.

Dosage forms can include solid or injectable implants or depots. In preferred embodiments, the implant comprises an effective amount of a warfarin neoglycoside and a biodegradable polymer. In preferred embodiments, a suitable biodegradable polymer can be selected from the group consisting of a polyaspartate, polyglutamate, poly(L-lactide), a poly(D, L-lactide), a poly(lactide-co-glycolide), a poly($\epsilon$-caprolactone), a polyanhydride, a poly(beta-hydroxy butyrate), a poly (ortho ester) and a polyphosphazene. In other embodiments, the implant comprises an effective amount of active agent and a silastic polymer. The implant provides the release of an effective amount of active agent for an extended period of about one week to several years.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

A tablet comprising the active ingredient can, for example, be made by compressing or molding the active ingredient, optionally with one or more additional ingredients. Compressed tablets can be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets can be made by molding, in a suitable device, a mixture of the active ingredient, a pharmaceutically acceptable carrier, and at least sufficient liquid to moisten the mixture. Pharmaceutically acceptable excipients used in the manufacture of tablets include inert diluents, granulating and disintegrating agents, binding agents, and lubricating agents. Known dispersing agents include potato starch and sodium starch glycolate. Known surface active agents include sodium lauryl sulfate. Known diluents include calcium carbonate, sodium carbonate, lactose, microcrystalline cellulose, calcium phosphate, calcium hydrogen phosphate, and sodium phosphate. Known granulating and disintegrating agents include corn starch and alginic acid. Known binding agents include gelatin, acacia, pre-gelatinized maize starch, polyvinylpyrrolidone, and hydroxypropyl methylcellulose. Known lubricating agents include magnesium stearate, stearic acid, silica, and talc.

Tablets can be non-coated or they can be coated using known methods to achieve delayed disintegration in the gastrointestinal tract of a human, thereby providing sustained release and absorption of the active ingredient. By way of example, a material such as glyceryl monostearate or glyceryl distearate can be used to coat tablets. Further by way of example, tablets can be coated using methods described in U.S. Pat. Nos. 4,256,108; 4,160,452; and 4,265,874 to form osmotically-controlled release tablets. Tablets can further comprise a sweetening agent, a flavoring agent, a coloring agent, a preservative, or some combination of these in order to provide pharmaceutically elegant and palatable preparation.

Solid dosage forms such as tablets, dragees, capsules, and granules can be prepared with coatings or shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in micro-encapsulated form, if appropriate, with one or more of the above-mentioned excipients.

Solid compositions of a similar type may also be used as fillers in soft or hard filled gelatin capsules using such excipients as lactose or milk sugar, as well as high molecular weight polyethylene glycols, and the like. Hard capsules comprising the active ingredient can be made using a physiologically degradable composition, such as gelatin. Such hard capsules comprise the active ingredient, and can further comprise additional ingredients including, for example, an inert solid diluent such as calcium carbonate, calcium phosphate, or kaolin. Soft gelatin capsules comprising the active ingredient can be made using a physiologically degradable composition, such as gelatin. Such soft capsules comprise the active ingredient, which can be mixed with water or an oil medium such as peanut oil, liquid paraffin, or olive oil.

Oral compositions can be made, using known technology, which specifically release orally-administered agents in the small or large intestines of a human patient. For example, formulations for delivery to the gastrointestinal system, including the colon, include enteric coated systems, based, e.g., on methacrylate copolymers such as poly(methacrylic acid, methyl methacrylate), which are only soluble at pH 6 and above, so that the polymer only begins to dissolve on entry into the small intestine. The site where such polymer formulations disintegrate is dependent on the rate of intestinal transit and the amount of polymer present. For example, a relatively thick polymer coating is used for delivery to the proximal colon (Hardy et al., 1987 Aliment. Pharmacol. Therap. 1:273-280). Polymers capable of providing site-specific colonic delivery can also be used, wherein the polymer relies on the bacterial flora of the large bowel to provide enzymatic degradation of the polymer coat and hence release of the drug. For example, azopolymers (U.S. Pat. No. 4,663, 308), glycosides (Friend et al., 1984, J. Med. Chem. 27:261-268) and a variety of naturally available and modified polysaccharides (see PCT application PCT/GB89/00581) can be used in such formulations.

Pulsed release technology such as that described in U.S. Pat. No. 4,777,049 can also be used to administer the active agent to a specific location within the gastrointestinal tract. Such systems permit drug delivery at a predetermined time and can be used to deliver the active agent, optionally together with other additives that my alter the local microenvironment to promote agent stability and uptake, directly to the colon, without relying on external conditions other than the presence of water to provide in vivo release.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, isotonic saline, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, almond oil, arachis oil, coconut oil, cottonseed oil, groundnut oil, corn germ oil, olive oil, castor oil, sesame seed oil, MIGLYOL™, glycerol, fractionated vegetable oils, mineral oils such as liquid paraffin, tetrahydrofurfuryl alcohol, polyethylene glycols, fatty acid esters of sorbitan, or mixtures of these substances, and the like. Besides such inert diluents, the composition can also include adjuvants, such as wetting agents, emulsifying and suspending agents, demulcents, preservatives, buffers, salts, sweetening, flavoring, coloring and perfuming agents. Suspensions, in addition to the active compound, may contain suspending agents, as for example, ethoxylated isostearyl alcohols, polyoxyethylene sorbitol or sorbitan esters, microcrystalline cellulose, hydrogenated edible fats, sodium alginate, polyvinylpyrrolidone, gum tragacanth, gum acacia, agar-agar, and cellulose derivatives such as sodium carboxymethylcellulose, methylcellulose, hydroxypropylmethylcellulose, aluminum metahydroxide, bentonite, or mixtures of these substances, and the like. Liquid formulations of a pharmaceutical composition of the invention that are suitable for oral administration can be prepared, packaged, and sold either in liquid form or in the form of a dry product intended for reconstitution with water or another suitable vehicle prior to use.

Known dispersing or wetting agents include naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include lecithin and acacia. Known preservatives include methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents can be prepared in substantially the same manner as liquid suspensions, the primary difference being that the active ingredient is dissolved, rather than suspended in the solvent. Liquid solutions of the pharmaceutical composition of the invention can comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

In other embodiments, the pharmaceutical composition can be prepared as a nutraceutical, i.e., in the form of, or added to, a food (e.g., a processed item intended for direct consumption) or a foodstuff (e.g., an edible ingredient intended for incorporation into a food prior to ingestion). Examples of suitable foods include candies such as lollipops, baked goods such as crackers, breads, cookies, and snack cakes, whole, pureed, or mashed fruits and vegetables, beverages, and processed meat products. Examples of suitable foodstuffs include milled grains and sugars, spices and other seasonings, and syrups.

Compositions for rectal or vaginal administration can be prepared by mixing a warfarin neoglycoside and any additional compounds with suitable non-irritating excipients or carriers such as cocoa butter, polyethylene glycol or a suppository wax, which are solid at ordinary room temperature, but liquid at body temperature, and therefore, melt in the rectum or vaginal cavity and release the warfarin neoglycoside. Such a composition can be in the form of, for example, a suppository, a retention enema preparation, and a solution for rectal or colonic irrigation. Suppository formulations can further comprise various additional ingredients including antioxidants and preservatives. Retention enema preparations or solutions for rectal or colonic irrigation can be made by combining the active ingredient with a pharmaceutically acceptable liquid carrier. As is known in the art, enema preparations can be administered using, and can be packaged within, a delivery device adapted to the rectal anatomy of a human. Enema preparations can further comprise various additional ingredients including antioxidants and preservatives.

A pharmaceutical composition of the invention can be prepared, packaged, or sold in a formulation suitable for vaginal administration. Such a composition can be in the form of, for example, a suppository, an impregnated or coated vaginally-insertable material such as a tampon, a douche preparation, or a solution for vaginal irrigation.

Dosage forms for topical administration of a warfarin neoglycoside include ointments, powders, sprays and inhalants. The compounds are admixed under sterile conditions with a physiologically acceptable carrier, and any preservatives, buffers, and/or propellants that may be required. Formulations suitable for topical administration include liquid or semi-liquid preparations such as liniments, lotions, oil-in-water or water-in-oil emulsions such as creams, ointments or pastes, and solutions or suspensions. Topically-administrable formulations can, for example, comprise from about 0.1% to about 10% (w/w) active ingredient, although the concentration of the active ingredient can be as high as the solubility limit of the active ingredient in the solvent. Formulations for topical administration can further comprise one or more of the additional ingredients described herein.

Ophthalmic formulations, eye ointments, powders, and solutions are also contemplated as being within the scope of this invention. Such formulations can, for example, be in the form of eye drops including, for example, a 0.1-1.0% (w/w) solution or suspension of the active ingredient in an aqueous or oily liquid carrier. Such drops can further comprise buffering agents, salts, or one or more other of the additional ingredients described herein. In other embodiments, ophthalmically administrable formulations comprise the active ingredient in microcrystalline form or in a liposomal preparation.

A pharmaceutical composition of the invention can be prepared, packaged, or sold in a formulation suitable for pulmonary administration via the buccal cavity. Such a formulation can comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant can be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point below 65 degrees F. at atmospheric pressure. Generally the propellant can constitute 50 to 99.9% (w/w) of the composition, and the active ingredient can constitute 0.1 to 20% (w/w) of the composition. The propellant can further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery can also provide the active ingredient in the form of droplets of a solution or suspension. Such formulations can be prepared, packaged, or sold as aqueous or dilute alcoholic solutions or suspensions, optionally sterile, comprising the active ingredient, and can conveniently be administered using any nebulization or atomization device. Such formulations can further comprise one or more additional ingredients including a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares. Formulations suitable for nasal administration can, for example, comprise from about as little as 0.1% (w/w) and as much as 100% (w/w)

of the active ingredient, and can further comprise one or more of the additional ingredients described herein.

A pharmaceutical composition of the invention can be prepared, packaged, or sold in a formulation suitable for buccal administration. Such formulations can, for example, be in the form of tablets or lozenges made using conventional methods, and can, for example, comprise 0.1 to 20% (w/w) active ingredient, the balance comprising an orally dissolvable or degradable composition and, optionally, one or more of the additional ingredients described herein. Alternately, formulations suitable for buccal administration can comprise a powder or an aerosolized or atomized solution or suspension comprising the active ingredient. Such powdered, aerosolized, or atomized formulations, when dispersed, preferably have an average particle or droplet size in the range from about 0.1 to about 200 nanometers, and can further comprise one or more of the additional ingredients described herein.

For parenteral administration in non-human animals, the compound or compounds may be prepared in the form of a paste or a pellet and administered as an implant, usually under the skin of the head or ear of the animal. Paste formulations can be prepared by dispersing a compound or compounds in pharmaceutically acceptable oil such as peanut oil, sesame oil, corn oil or the like. Pellets containing a therapeutically effective amount of a compound or compounds can be prepared by admixing the compound with a diluent such as a carbowax, carnauba wax, and the like, and a lubricant, such as magnesium or calcium stearate, can be added to improve the pelleting process. It is, of course, recognized that more than one pellet may be administered to an animal to achieve the desired dose level. Moreover, it has been found that such implants may also be administered periodically during the animal treatment period in order to maintain the proper active agent level in the animal's body.

The warfarin neoglycoside of the present invention, the stereoisomers and prodrugs thereof, and the pharmaceutically acceptable salts of the peptides, stereoisomers, and prodrugs, can be administered to a patient at dosage levels in the range of from about 0.01 to about 1,000 mg per day. For a normal adult human having a body weight of about 70 kg, a dosage in the range of from about 0.01 to about 300 mg is typically sufficient. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

It is not critical whether the compound is administered directly to the cell, to a tissue comprising the cell, a body fluid that contacts the cell, or a body location from which the compound can diffuse or be transported to the cell. It is sufficient that the compound is administered to the patient in an amount and by a route whereby an amount of the compound sufficient to mobilize lipids in the cell arrives, directly or indirectly at the cell. The minimum amount varies with the identity of the warfarin neoglycoside. In some embodiments, the minimum amount is generally in the range from $10^{-9}$ to $10^{-5}$ molar. In other embodiments, the minimum amount is typically in the range from $10^{-7}$ to $10^{-5}$ molar.

In preferred embodiments, a pharmaceutical composition comprising a warfarin neoglycoside can be administered to a patient at dosage levels in the range of about 0.1 to about 7,000 mg per day. A preferred dosage range is about 1 to about 100 mg per day. In other embodiments, a pharmaceutical composition comprising a neoglycoside can be administered to deliver a dose of between 1 nanogram per day per kilogram body weight and 100 milligrams per day per kilogram body weight, preferably from about 0.1 to about 10 mg/kg body weight of the individual per day, and preferably to deliver of between 100 milligrams and 2 grams, to a human patient.

The specific dosage and dosage range that can be used depends on a number of factors, including the requirements of the patient, the severity of the condition or disease being treated, and the pharmacological activity of the compound being administered. The determination of dosage ranges and optimal dosages for a particular patient is well within the ordinary skill of one in the art in view of this disclosure. It is understood that the ordinarily skilled physician or veterinarian will readily determine and prescribe an effective amount of the compound to mobilize lipid stores, induce weight loss, or inhibit appetite in the patient. In so proceeding, the physician or veterinarian can, for example, prescribe a relatively low dose at first, subsequently increasing the dose until an appropriate response is obtained. It is further understood, however, that the specific dose level for any particular human will depend upon a variety of factors including the activity of the specific compound employed, the age, body weight, general health, gender, and diet of the human, the time of administration, the route of administration, the rate of excretion, any drug combination, and the severity of any disorder being treated.

In some embodiments, a warfarin neoglycoside of the present invention, a stereoisomer or prodrug thereof, or a pharmaceutically acceptable salt of the stereoisomer or prodrug; is administered to a subject in need of treatment therewith, preferably in the form of a pharmaceutical composition. It is generally preferred that such administration be oral or pulmonary. However, if the subject being treated is unable to swallow, or oral administration is otherwise impaired or undesirable, parenteral or transdermal administration will be appropriate.

Warfarin is strongly fluorescent. Thus, in a third aspect, the invention encompasses methods for assaying sugar uptake in cells. Such methods include the steps of contacting cells with a warfarin neoglycoside as described above, and measuring the uptake of the neoglycoside into the cells.

In preferred embodiments, the step of measuring the uptake of the neoglycoside is performed by a fluorescence-based assay. Fluorescence-based assays are well known in the art, and examples of fluorescence based techniques that could be used in the present method include fluorescence microscopy and micro-imaging, time-resolved microspectrofluorimetry, the use of fluorescence activated cell sorter (FACS) instrumentation, and the use of florescence-based microarrays.

While this invention has been described in conjunction with the various exemplary embodiments outlined in the Examples below, various alternatives, modifications, variations, improvements and/or substantial equivalents, whether known or that are or may be presently unforeseen, may become apparent to those having at least ordinary skill in the art.

3. Examples

Example 1

Synthesis and Characterization of Warfarin Neoglycosides

Figure 2:
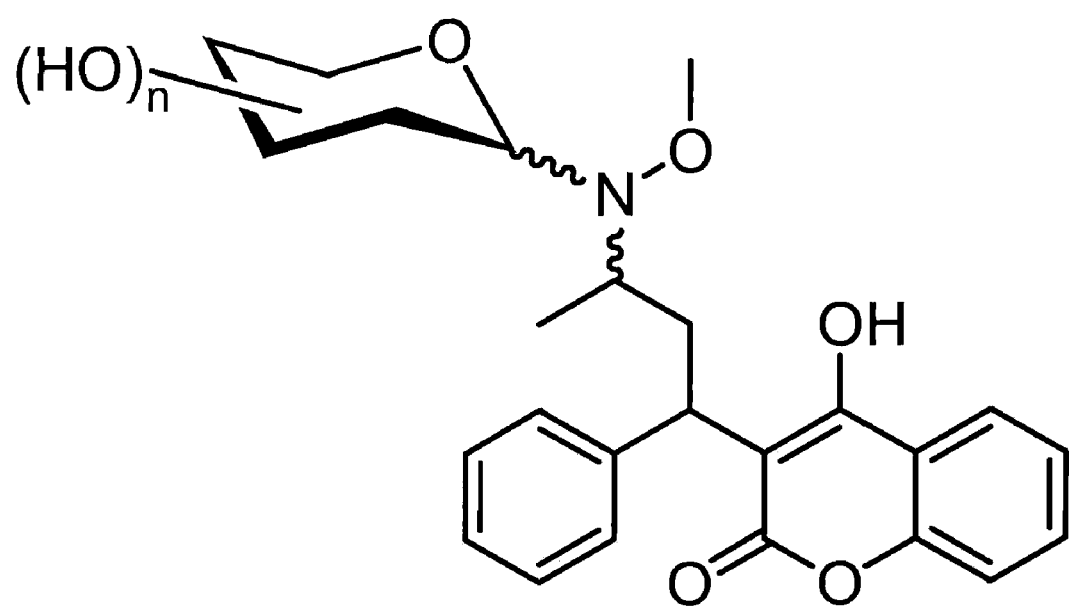
FIG. 2 shows the general chemical structure of the warfarin neoglycosides of the present invention.

In this Example, Applicants report the synthesis and characterization of the novel warfarin neoglycosides of the present invention. Specifically, 51 different warfarin neoglycosides were synthesized and 38 were successfully characterized. Warfarin (FIG. 1) was used as a starting material in a three step process yielding the novel warfarin neoglycosides reported herein (FIG. 2). FIG. 3 shows the general scheme used in the synthesis.

General Methods

All chemicals and solvents were purchased commercially and used without further purification unless otherwise specified. Analytical thin-layer chromatography was performed using aluminum-backed TLC plates pre-coated with silica gel (Sigma-Aldrich, 200 µm layer thickness, 25 µM particle size) and compounds were detected by UV absorbance (254 nm). Automated normal-phase flash chromatography was performed using an Isco CombiFlash® Sg 100c Separation System. Warfarin neoglycosides were purified using this system equipped with RediSep® $R_f$ silica flash columns (4 g) at a flow-rate of 20 mL/min and one of the following gradients (where A=EtOAc and B=hexanes): 0/100 A:B (0 min)→10/90 A:B (20 min)→0/100 A:B (25 min) (hereafter denoted as Method A) or 0/100 A:B (0 min)→20/80 A:B (20 min)→0/100 A:B (25 min) (hereafter denoted as Method B).

Melting points were measured in open capillary tubes using a Mel-Temp melting point apparatus and are reported uncorrected. NMR data was collected using a Varian Unity-Inova 400 MHz spectrometer. Chemical shifts are reported in parts per million relative to a tetramethylsilane internal standard at 0.00 ppm for samples dissolved in $CDCl_3$, while spectra recorded in DMSO were referenced to the solvent peak.

Electrospray ionization mass spectra were obtained using a Waters (Micromass) LCT™ instrument with a time-of-flight analyzer. For exact mass measurements (EMM), an aliquot of a known compound (lock mass) was added to the sample. Liquid chromatography-mass spectrometry (LC-MS) analysis was conducted using electrospray ionization on an Agilent 1100 HPLC-MSD SL quadrupole mass spectrometer connected to a diode array detector. For LC-MS analysis, samples were analyzed by analytical HPLC using a Phenomenex Gemini 5 µm C18 110 Å reversed-phase column (250×4.6 mm) at a flow-rate of 1 mL/min with the following gradient (where A=Milli-Q $H_2O$ containing 0.1% v/v formic acid and B=acetonitrile): 90/10 A:B (0 min)→25/75 A:B (20 min)→0/100 A:B (21 min)→0/100 A:B (26 min)→90/10 A:B (29 min)→90/10 (35 min). HPLC peak areas were integrated and the purity of each compound calculated as a percentage of the total peak area. Analytical HPLC of purified products was performed using a Varian ProStar instrument and the same conditions as for LC-MS analysis except that solvent A=Milli-Q $H_2O$ containing 0.1% v/v trifluoroacetic acid in lieu of formic acid. Compounds were monitored at an absorbance of 254 nm.

Figure 5:
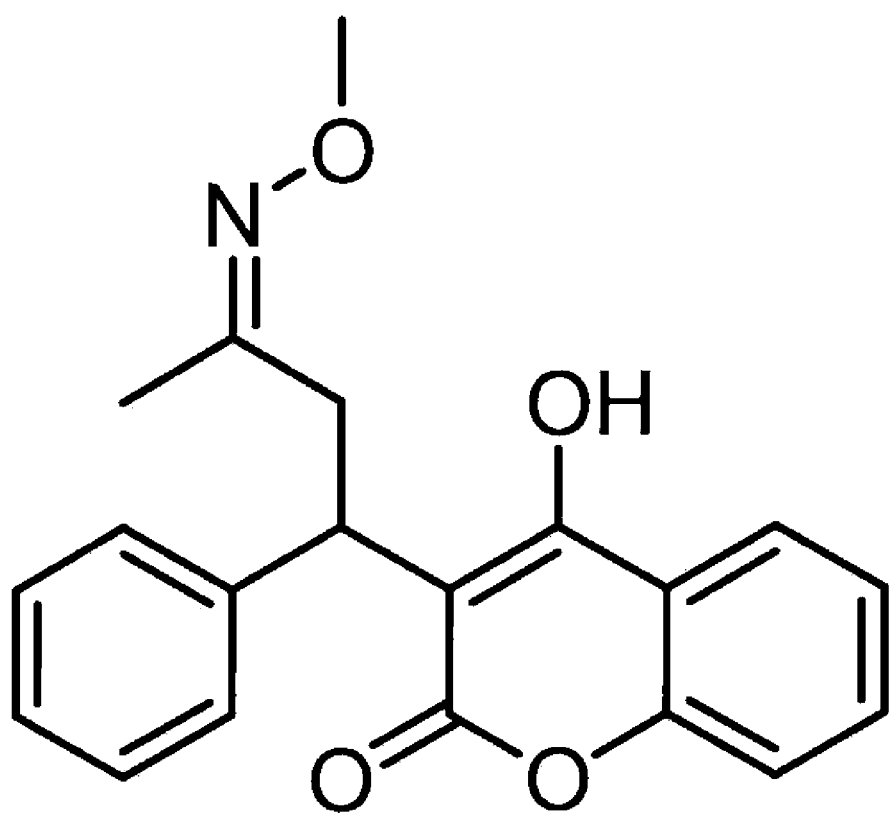
FIG. 5 shows the chemical structure of the warfarin analog oxime 4-hydroxy-3-(3-(methoxyimino)-1-phenylbutyl)-2H-1-benzopyran-2-one, which is the first intermediate of the general synthesis strategy used to synthesize the warfarin neoglycosides of the present invention. This warfarin analog oxime is produced from warfarin in the first step of the general synthesis strategy, and reacts further in the second step of the general synthesis strategy to produce the warfarin analog aglycon shown in FIG. 4.

Preparation and characterization of 4-hydroxy-3-(3-(methoxyimino)-1-phenylbutyl)-2H-1-benzopyran-2-one (warfarin analog oxime; FIG. 5). Warfarin (5.00 g, 16.2 mmol) was dissolved in HPLC-grade MeOH (240 mL) in a round-bottomed flask. Pyridine (2.9 mL, 36 mmol) and methoxylamine hydrochloride (2.16 g, 25.9 mmol) were added and the resulting solution was stirred at room temperature for 18 h. The reaction mixture was concentrated under reduced pressure and the resulting residue was dissolved in $CH_2Cl_2$ (250 mL). Following extraction with 1 M aq HCl (3×150 mL) and saturated aq NaCl (250 mL), the organic layer was dried over $MgSO_4$, filtered, and concentrated under reduced pressure to afford a white solid (5.43 g, 16.1 mmol, 99% yield). This product (TLC $R_f$=0.44 in 1:1 EtOAc/hexanes) was used without further purification.

The following is the melting point and spectral data for the resulting product: mp 94-96° C.; $^1H$ NMR (400 MHz, $CDCl_3$): δ 7.94 (dd, J=1.6, 8.0 Hz, 1H, Ph), 7.51-7.44 (m, 1H, Ph), 7.37-7.15 (m, 7H, Ph), 4.74 (dd, 1H, J=1.6, 11.2 Hz, CH), 3.93 (s, 3H, $OCH_3$), 3.51 (dd, 1H, J=11.0, 18.6 Hz, $CH_2$), 3.12 (dd, 1H, J=1.8, 18.6 Hz, $CH_2$), 1.95 (s, 3H, $CH(CH_3)$); $^{13}C$ NMR (100 MHz, $CDCl_3$): δ 162.0, 161.0, 159.5, 153.1, 141.0, 131.6, 128.3, 128.1, 126.6, 124.0, 123.8, 117.4, 116.4, 109.0, 61.4, 37.9, 35.7, 16.5; HRMS-ESI (m/z): [M-H]⁻ calculated for $C_{20}H_{18}NO_4$, 336.1241; found, 336.1243.

Figure 6:
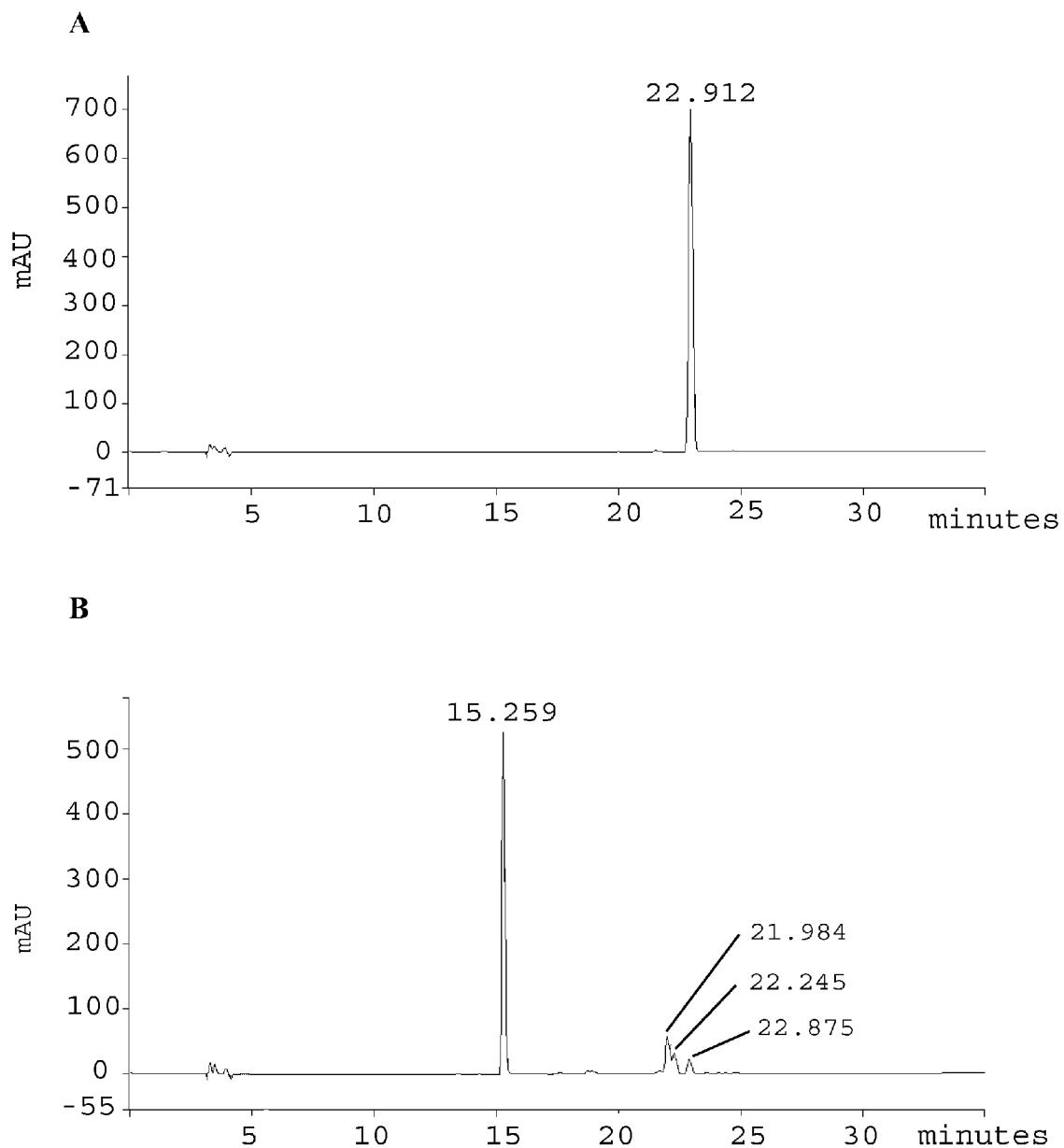
FIG. 6 shows high performance liquid chromatography (HPLC) traces of the purified warfarin analog oxime having the structure shown in FIG. 5 (FIG. 6A) and the purified warfarin analog aglycon having the structure shown in FIG. 4 (FIG. 6B), run on a Phenomenex Gemini 5 μm C18 110 Å reversed-phase column.
Figure 7:
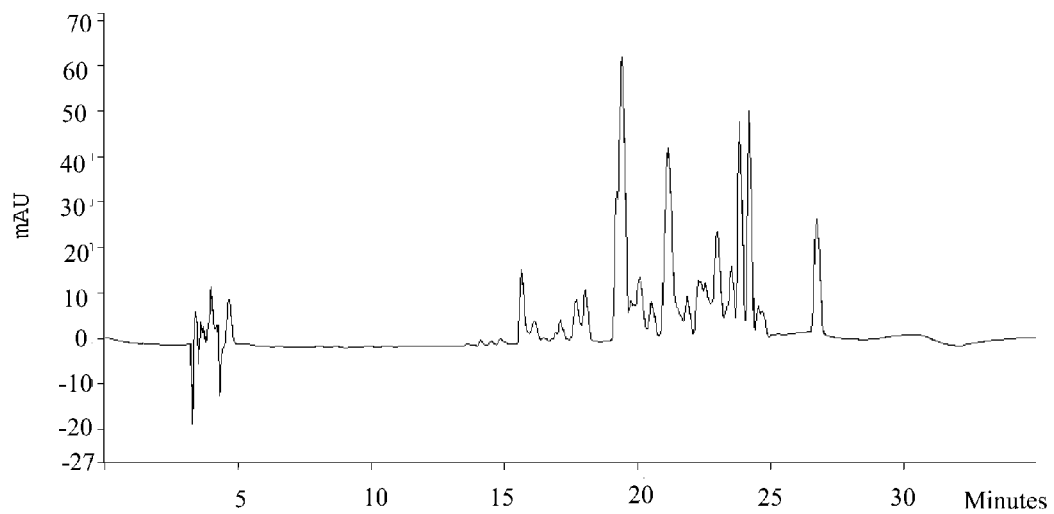
FIG. 7 shows HPLC traces of purified warfarin neoglycosides having the general structure shown in FIG. 2, run on a Phenomenex Gemini 5 μm C18 110 Å reversed-phase column.
Figure 7:
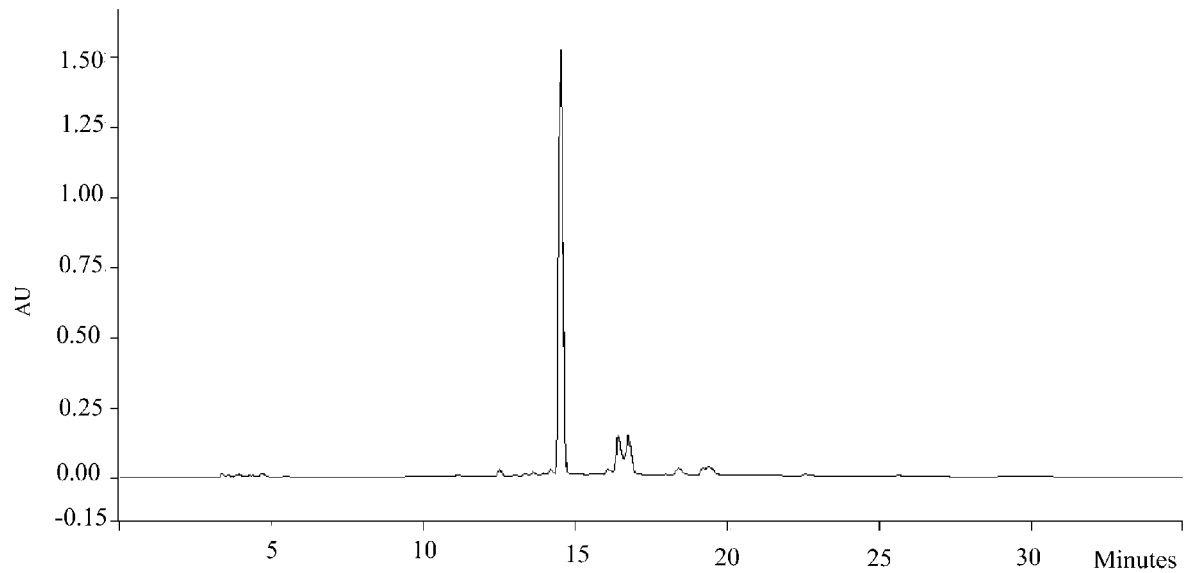
Figure 8:
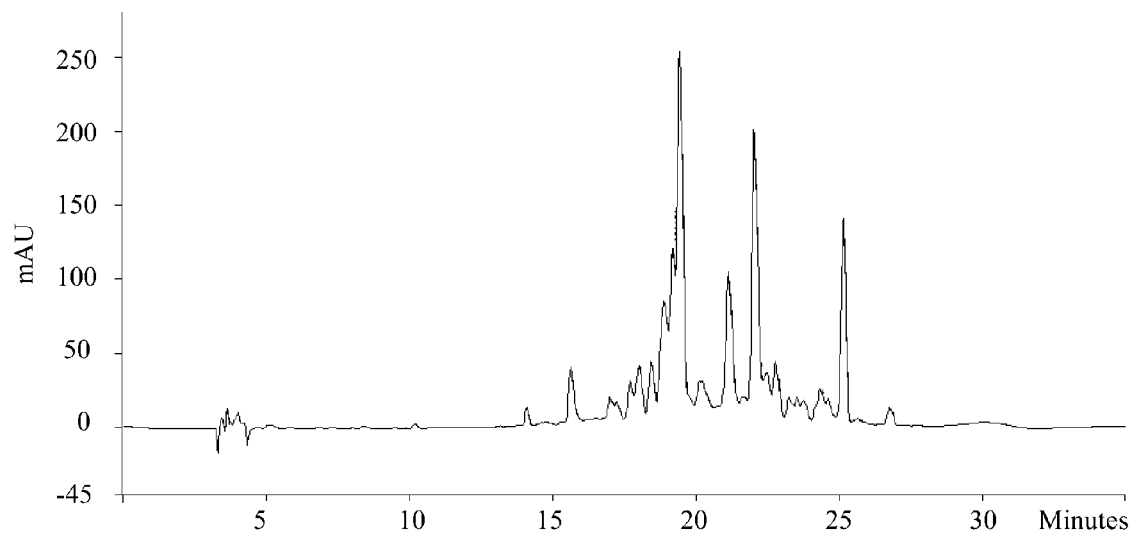
FIG. 8 shows HPLC traces of purified warfarin neoglycosides having the general structure shown in FIG. 2, run on a Phenomenex Gemini 5 μm C18 110 Å reversed-phase column.
Figure 8:
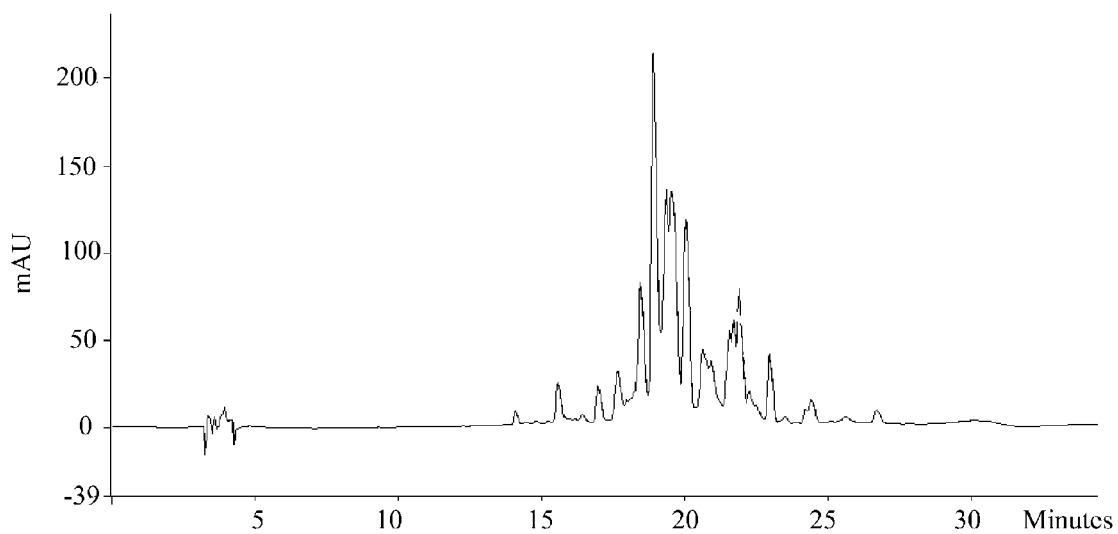
Figure 9:
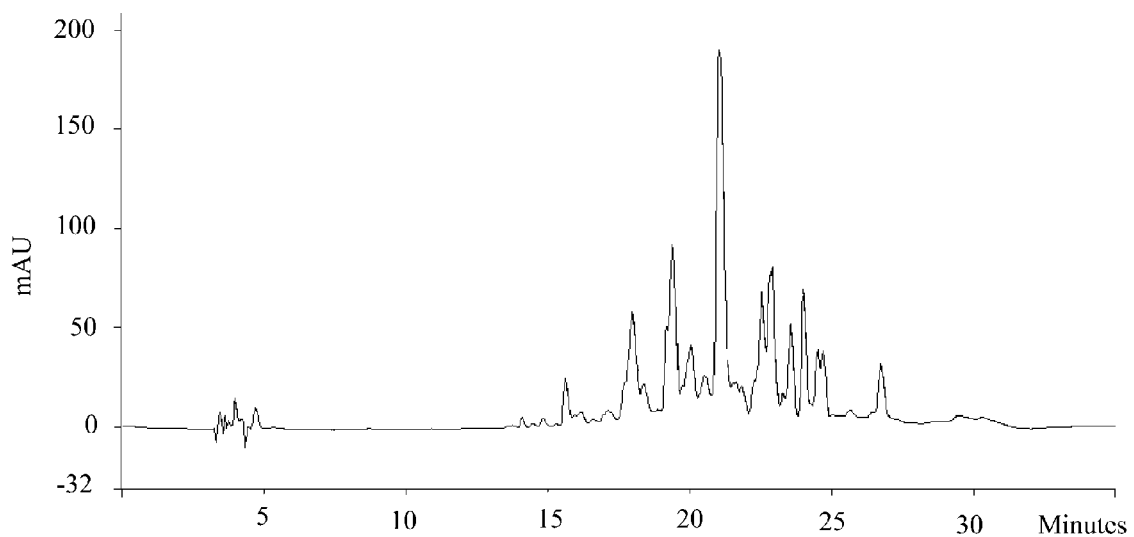
FIG. 9 shows HPLC traces of purified warfarin neoglycosides having the general structure shown in FIG. 2, run on a Phenomenex Gemini 5 μm C18 110 Å reversed-phase column.
Figure 9:
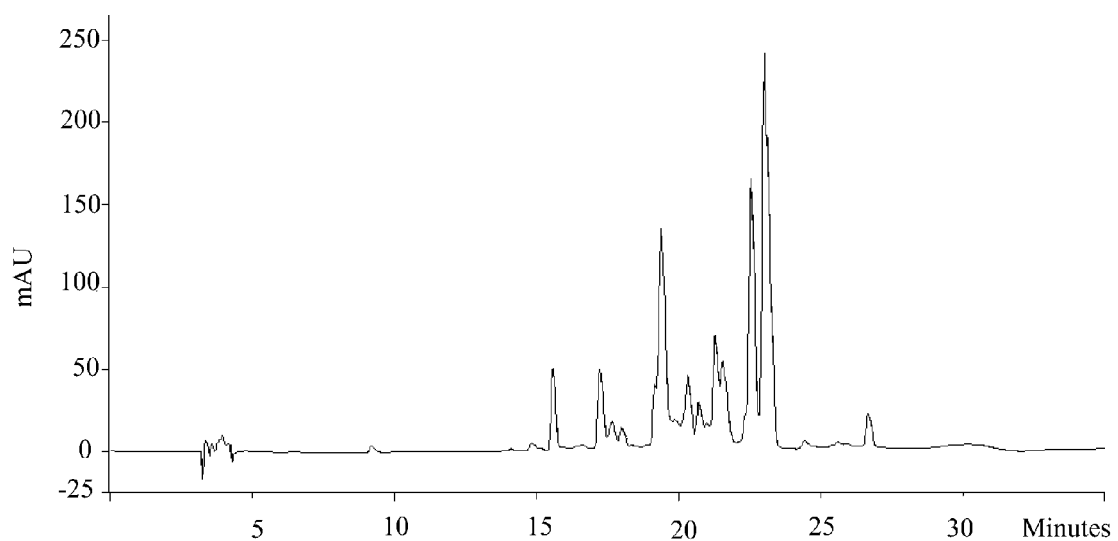
Figure 10:
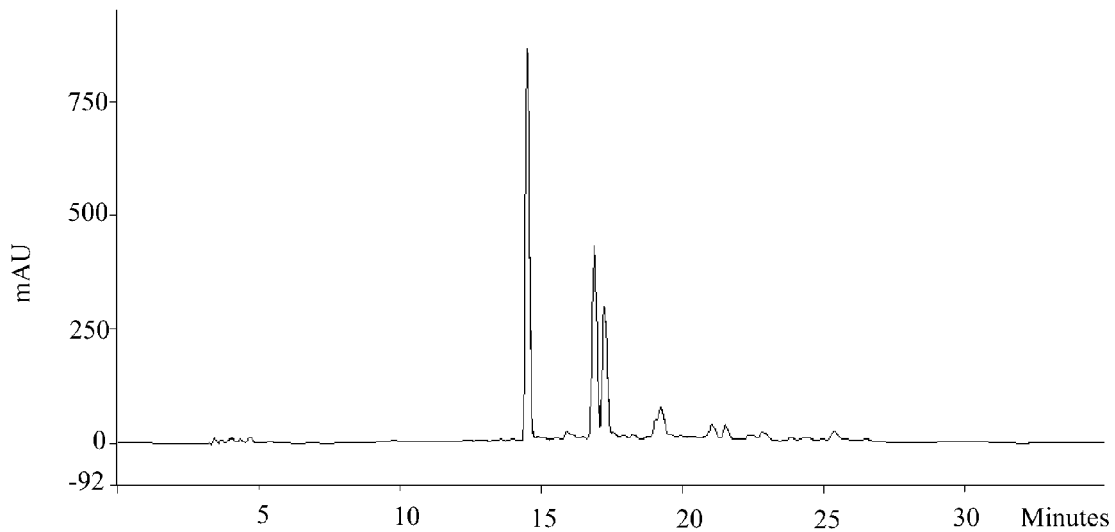
FIG. 10 shows HPLC traces of purified warfarin neoglycosides having the general structure shown in FIG. 2, run on a Phenomenex Gemini 5 μm C18 110 Å reversed-phase column.
Figure 10:
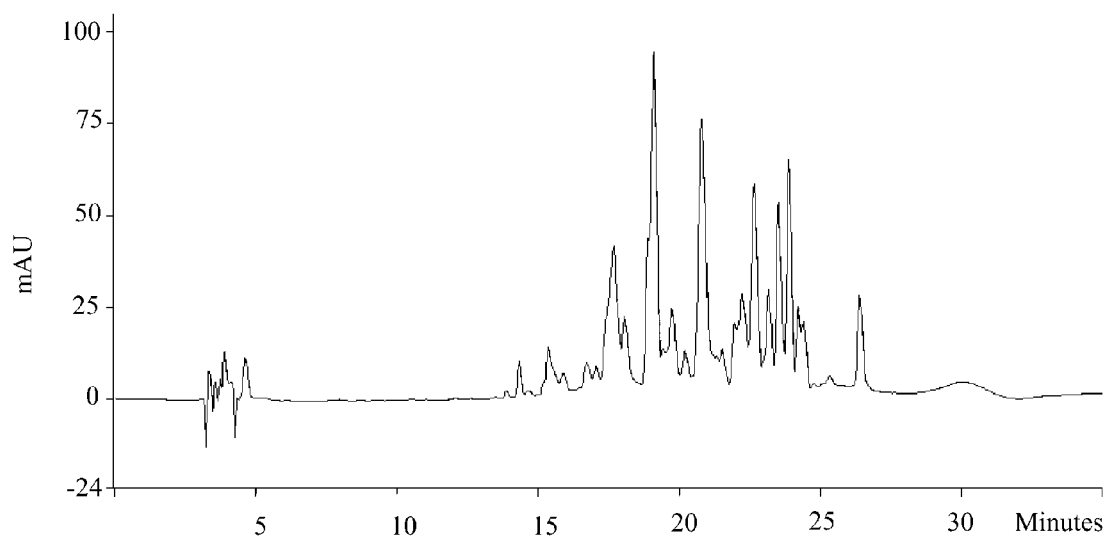
Figure 11:
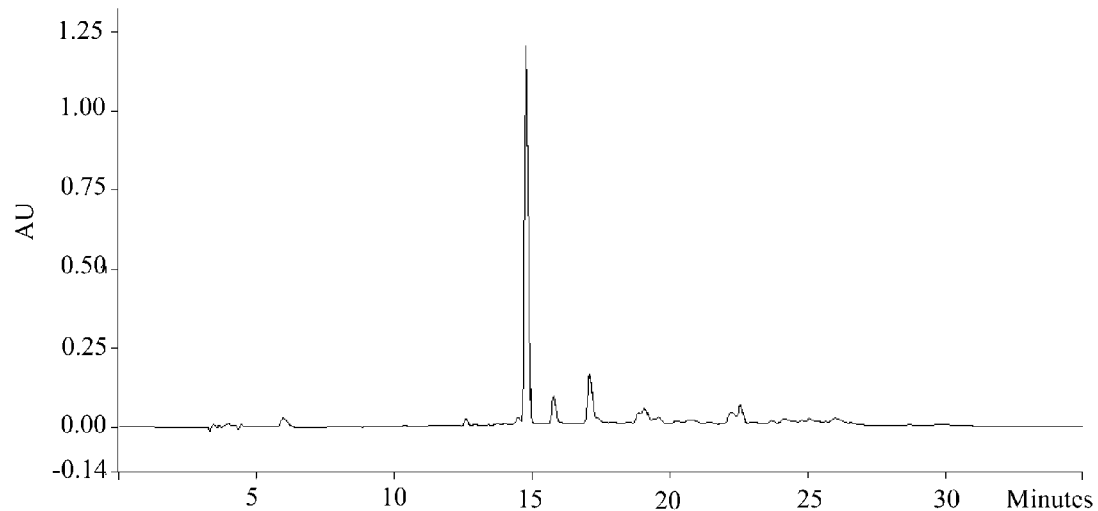
FIG. 11 shows HPLC traces of purified warfarin neoglycosides having the general structure shown in FIG. 2, run on a Phenomenex Gemini 5 μm C18 110 Å reversed-phase column.
Figure 11:
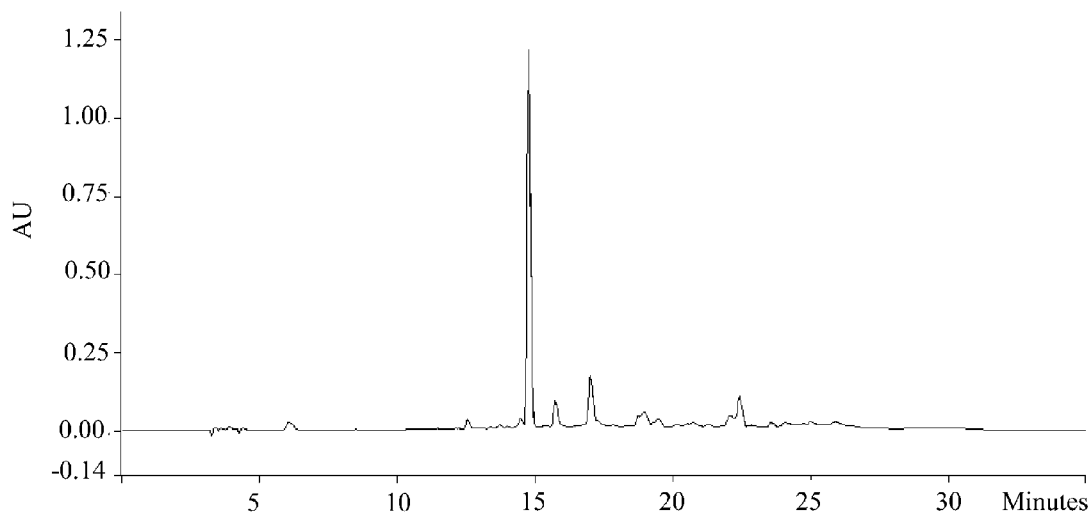
Figure 12:
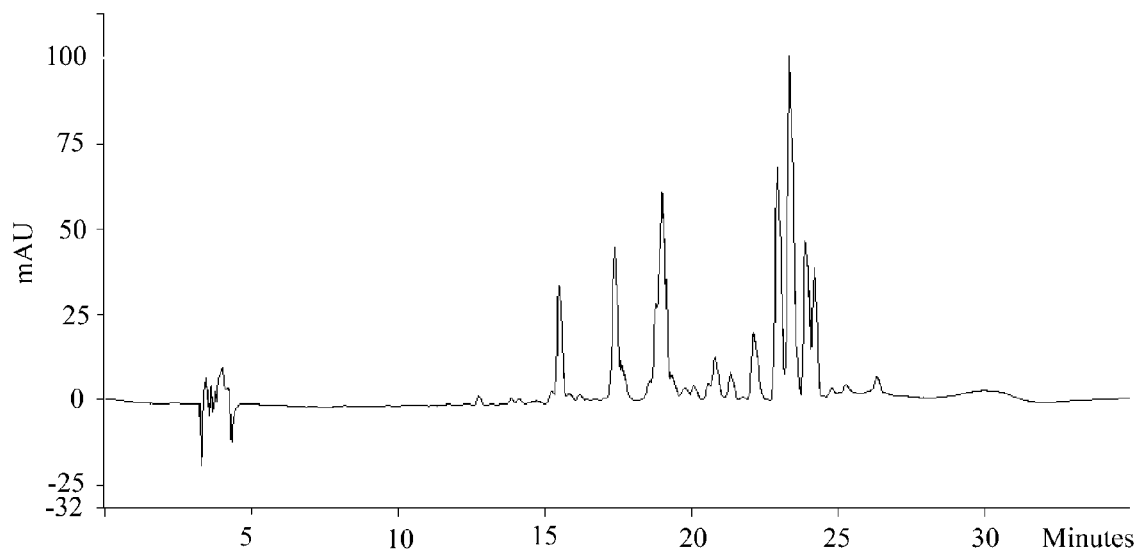
FIG. 12 shows HPLC traces of purified warfarin neoglycosides having the general structure shown in FIG. 2, run on a Phenomenex Gemini 5 μm C18 110 Å reversed-phase column.
Figure 12:
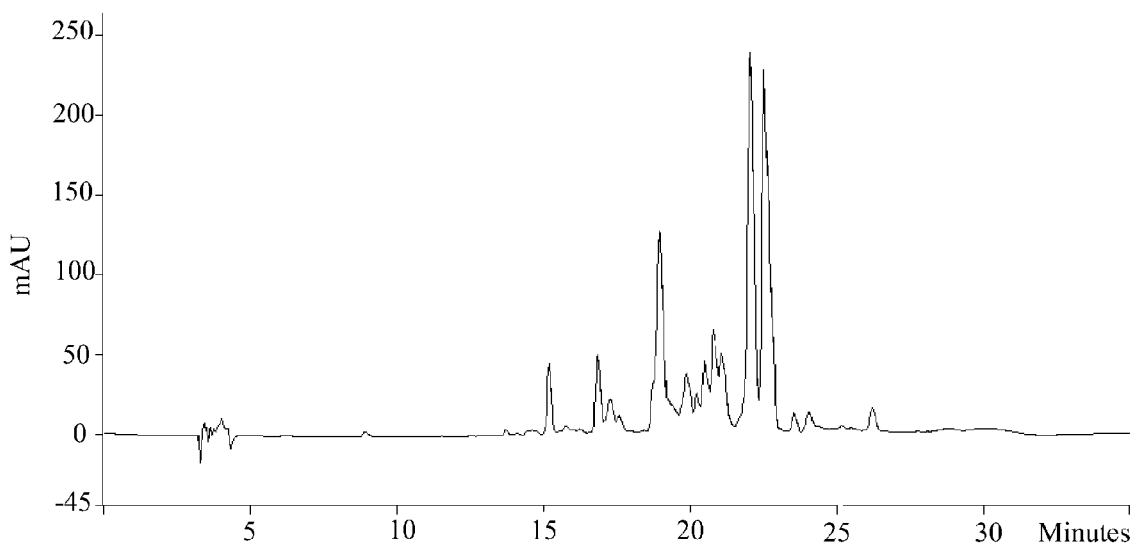
Figure 13:
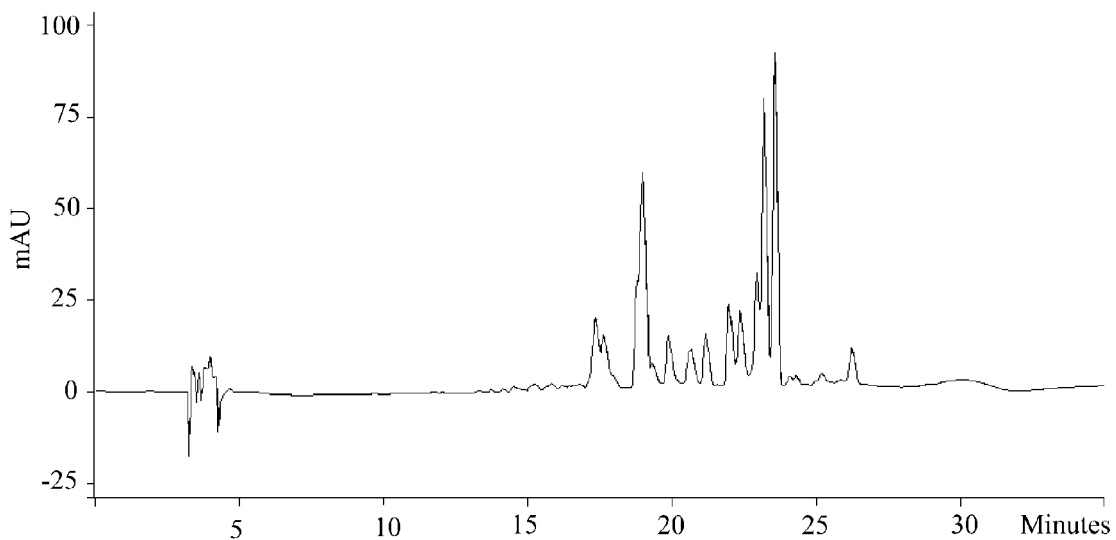
FIG. 13 shows HPLC traces of purified warfarin neoglycosides having the general structure shown in FIG. 2, run on a Phenomenex Gemini 5 μm C18 110 Å reversed-phase column.
Figure 13:
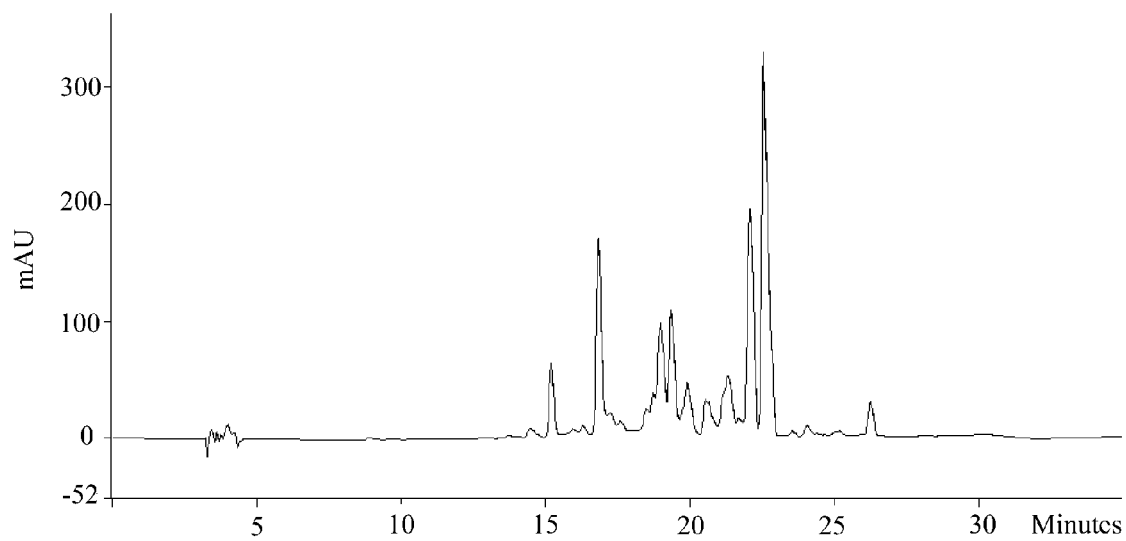
Figure 14:
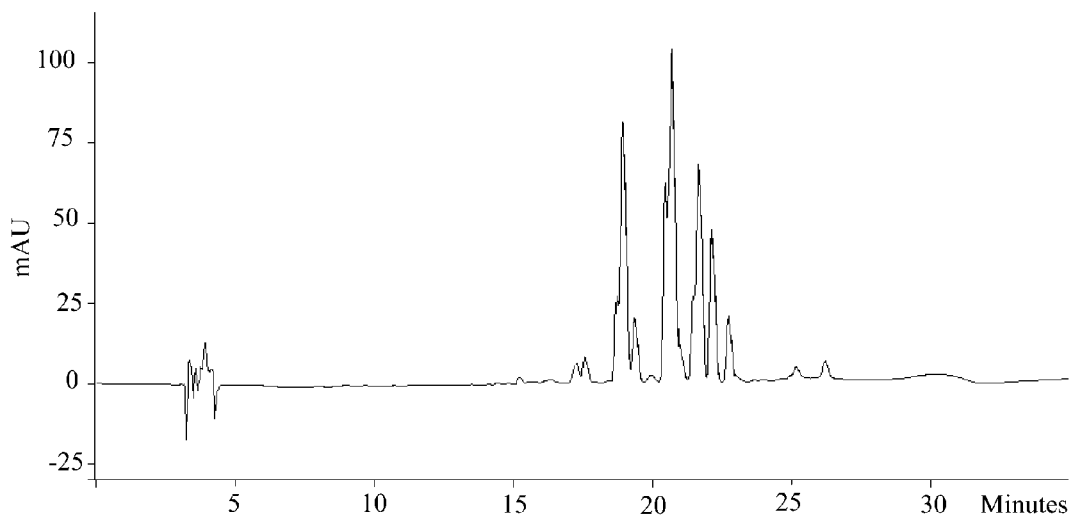
FIG. 14 shows HPLC traces of purified warfarin neoglycosides having the general structure shown in FIG. 2, run on a Phenomenex Gemini 5 μm C18 110 Å reversed-phase column.
Figure 14:
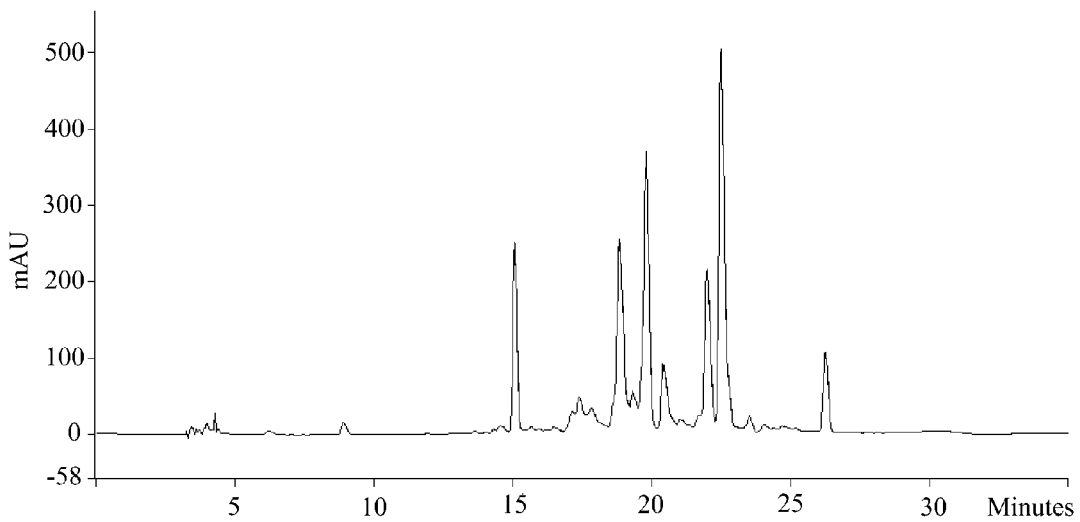
Figure 15:
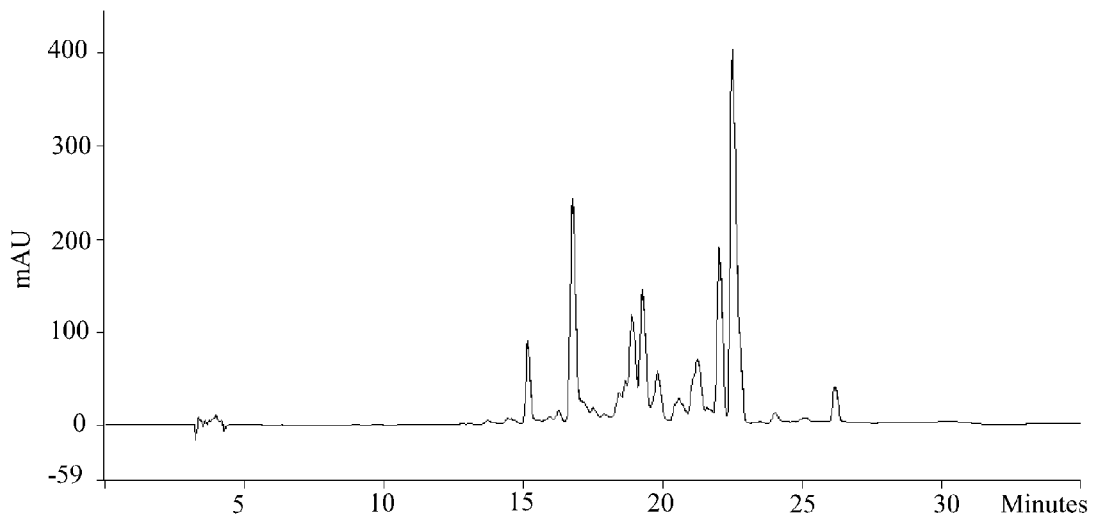
FIG. 15 shows HPLC traces of purified warfarin neoglycosides having the general structure shown in FIG. 2, run on a Phenomenex Gemini 5 μm C18 110 Å reversed-phase column.
Figure 15:
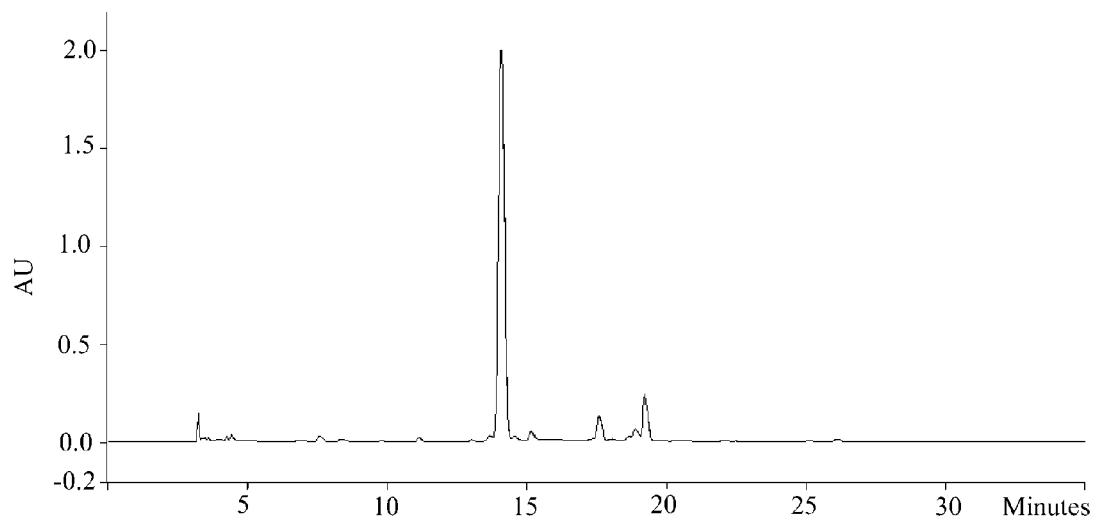
Figure 16:
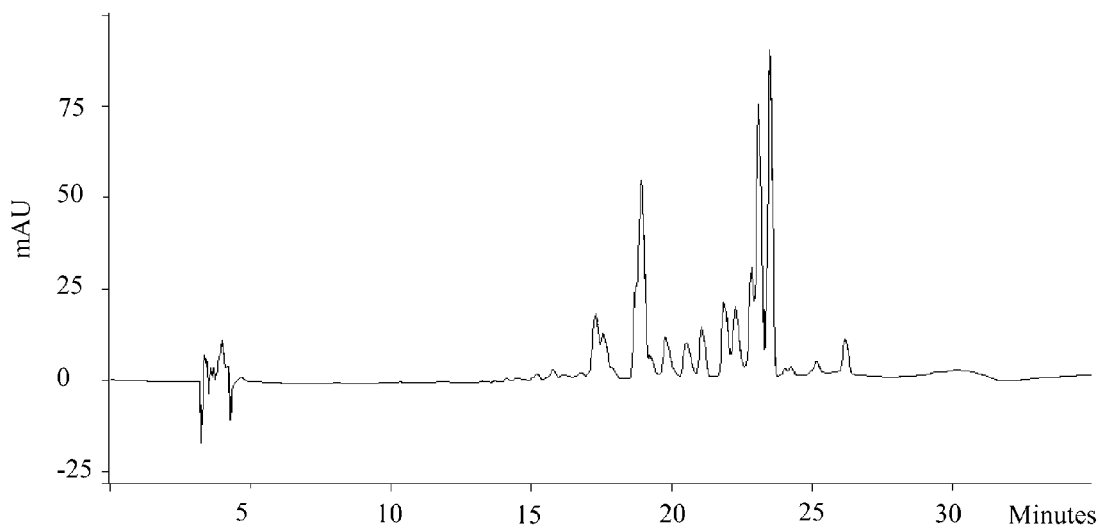
FIG. 16 shows HPLC traces of purified warfarin neoglycosides having the general structure shown in FIG. 2, run on a Phenomenex Gemini 5 μm C18 110 Å reversed-phase column.
Figure 16:
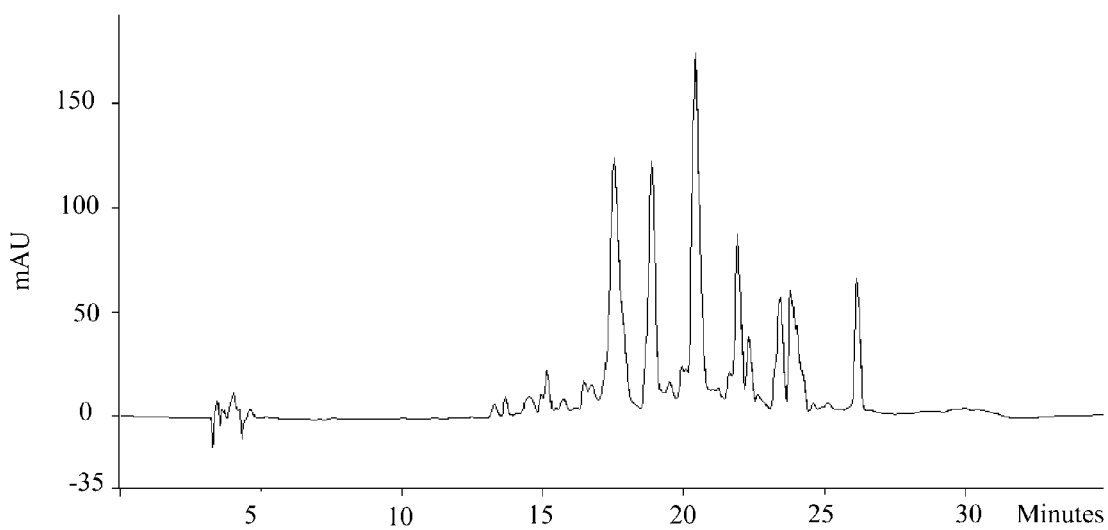
Figure 17:
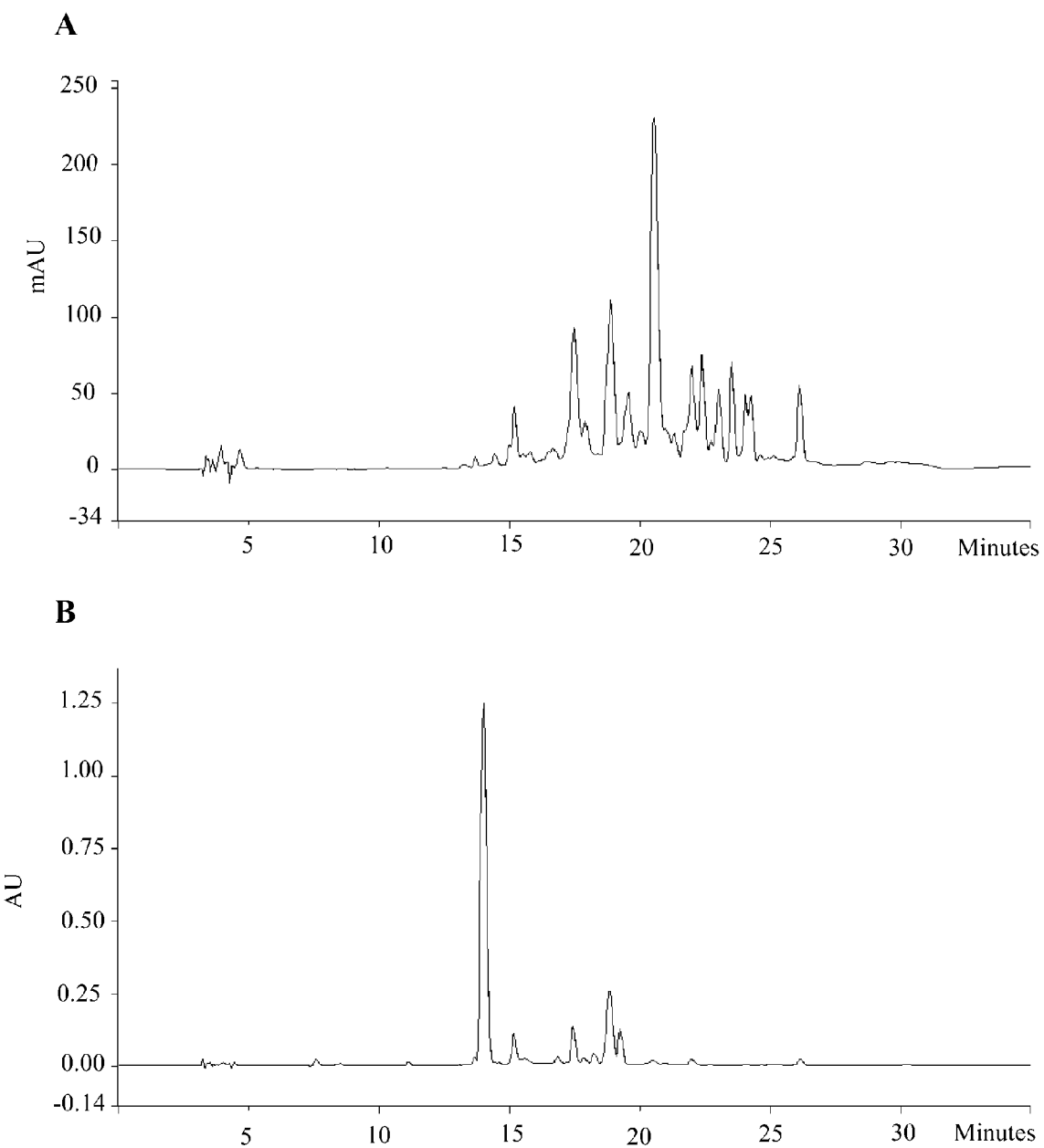
FIG. 17 shows HPLC traces of purified warfarin neoglycosides having the general structure shown in FIG. 2, run on a Phenomenex Gemini 5 μm C18 110 Å reversed-phase column.
Figure 18:
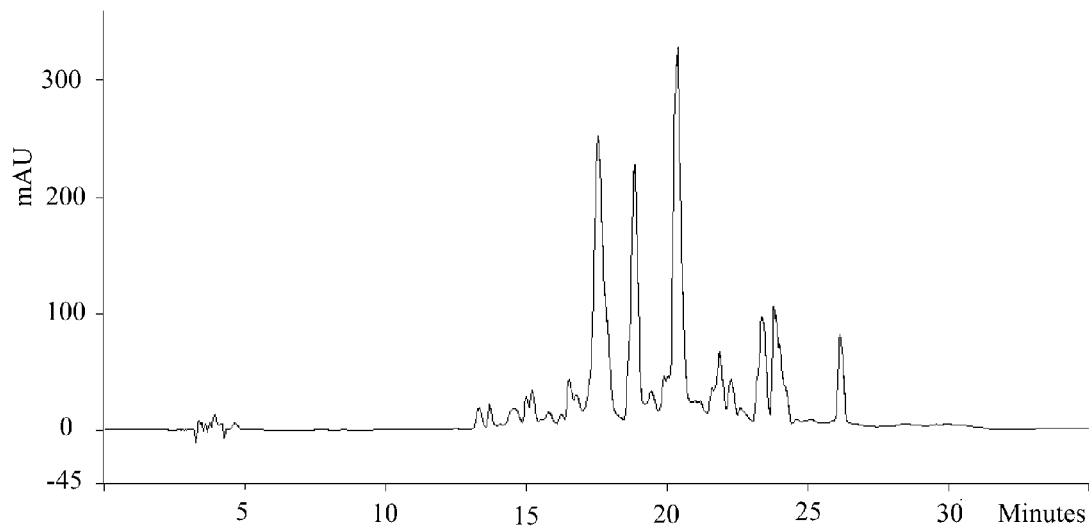
FIG. 18 shows HPLC traces of purified warfarin neoglycosides having the general structure shown in FIG. 2, run on a Phenomenex Gemini 5 μm C18 110 Å reversed-phase column.
Figure 18:
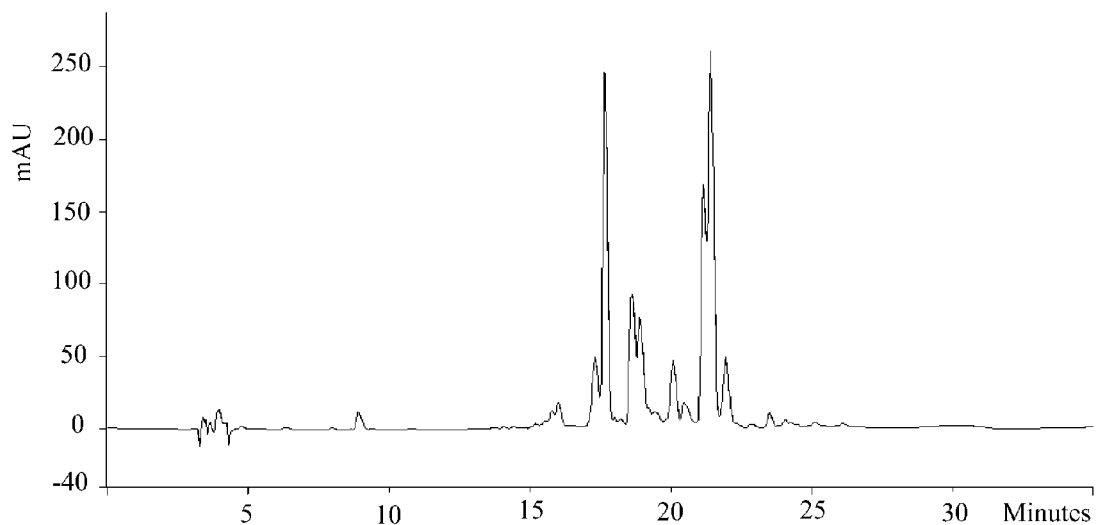
Figure 19:
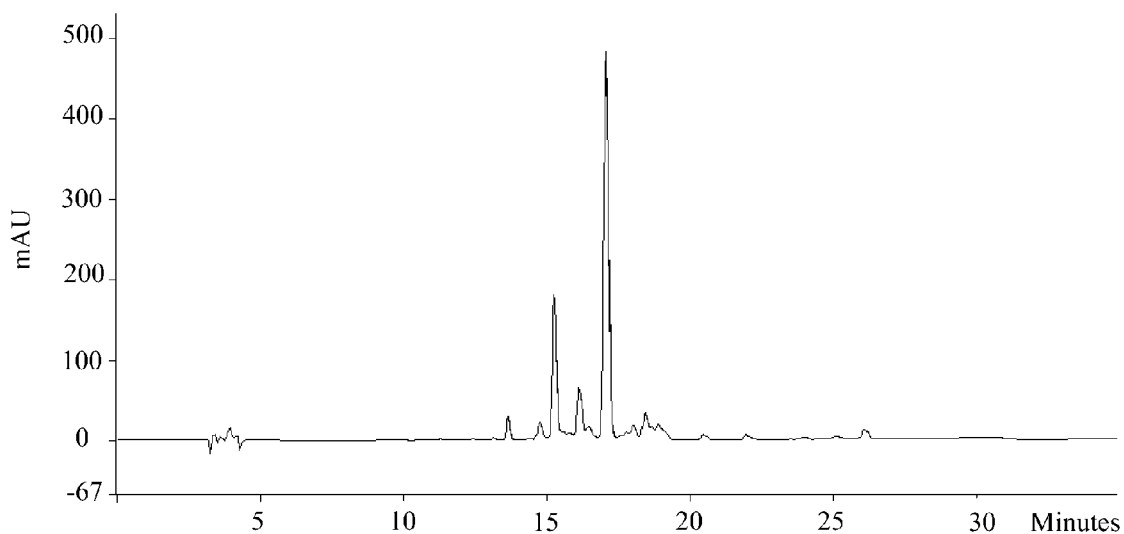
FIG. 19 shows HPLC traces of purified warfarin neoglycosides having the general structure shown in FIG. 2, run on a Phenomenex Gemini 5 μm C18 110 Å reversed-phase column.
Figure 19:
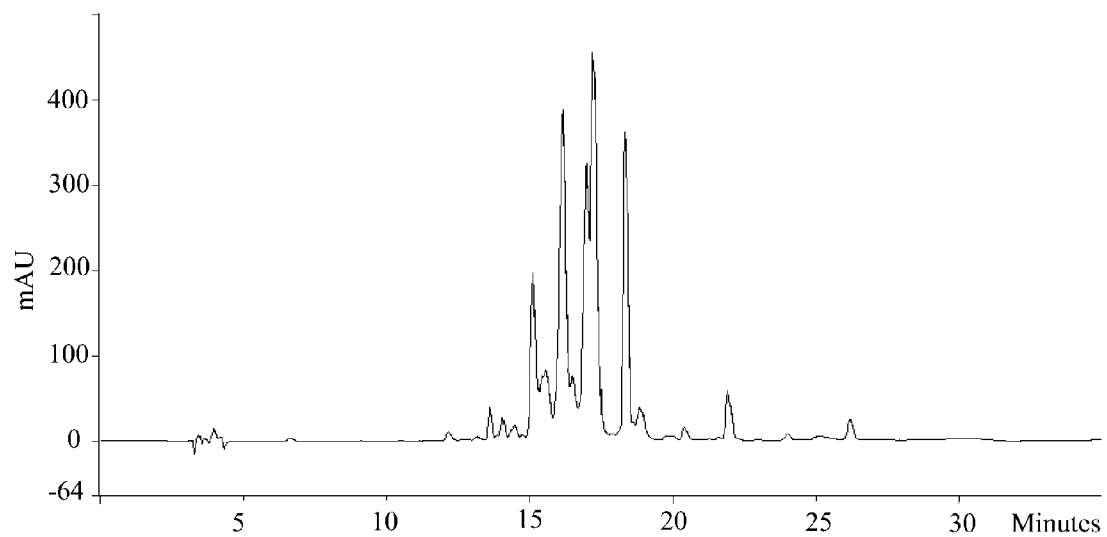
Figure 20:
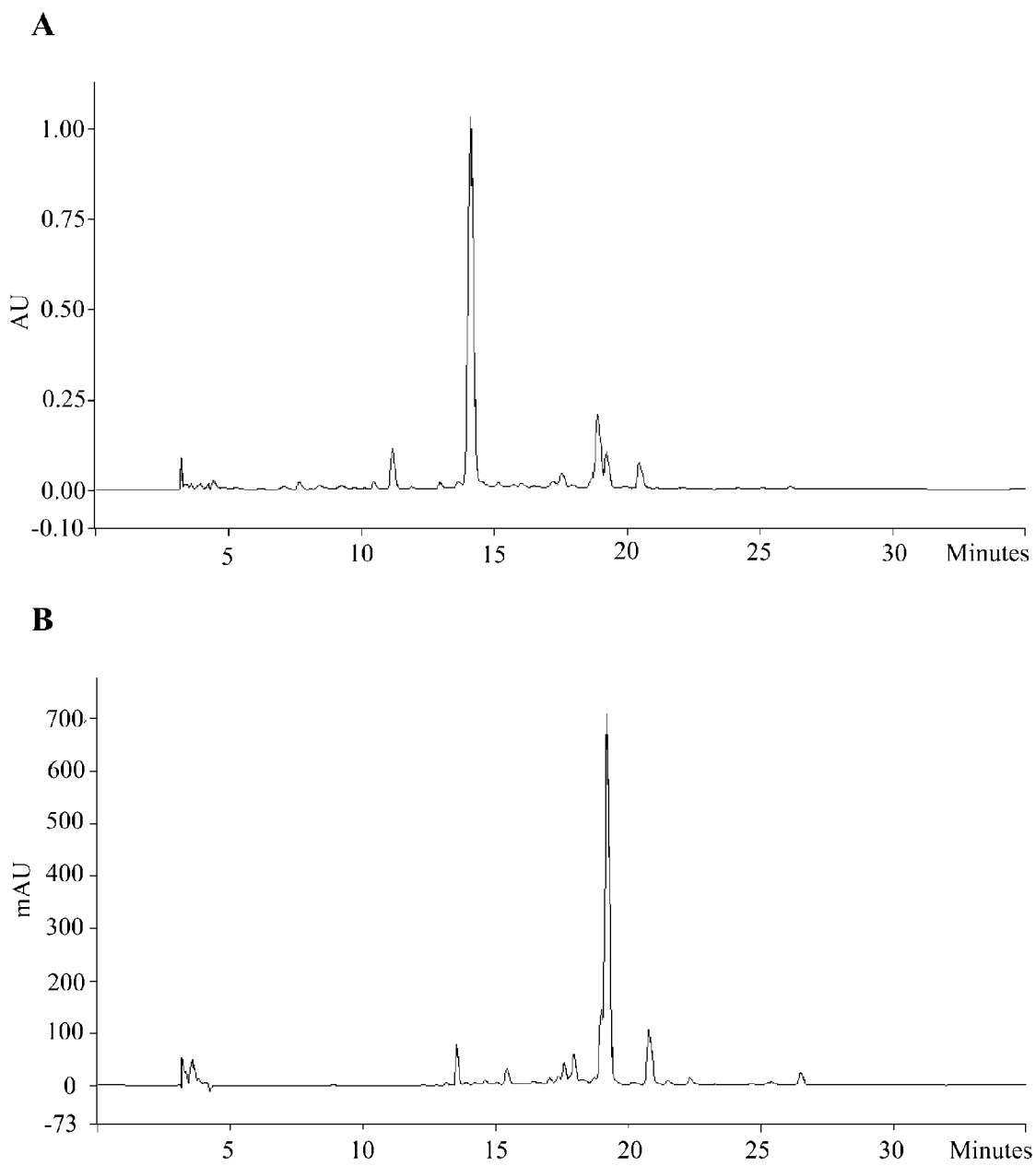
FIG. 20 shows HPLC traces of purified warfarin neoglycosides having the general structure shown in FIG. 2, run on a Phenomenex Gemini 5 μm C18 110 Å reversed-phase column.
Figure 21:
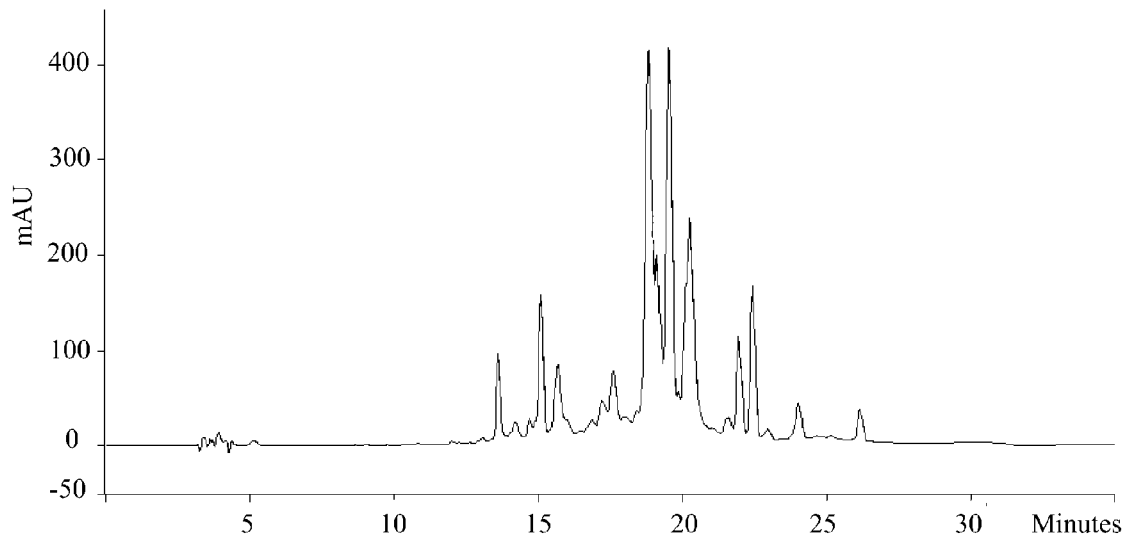
FIG. 21 shows HPLC traces of purified warfarin neoglycosides having the general structure shown in FIG. 2, run on a Phenomenex Gemini 5 μm C18 110 Å reversed-phase column.
Figure 21:
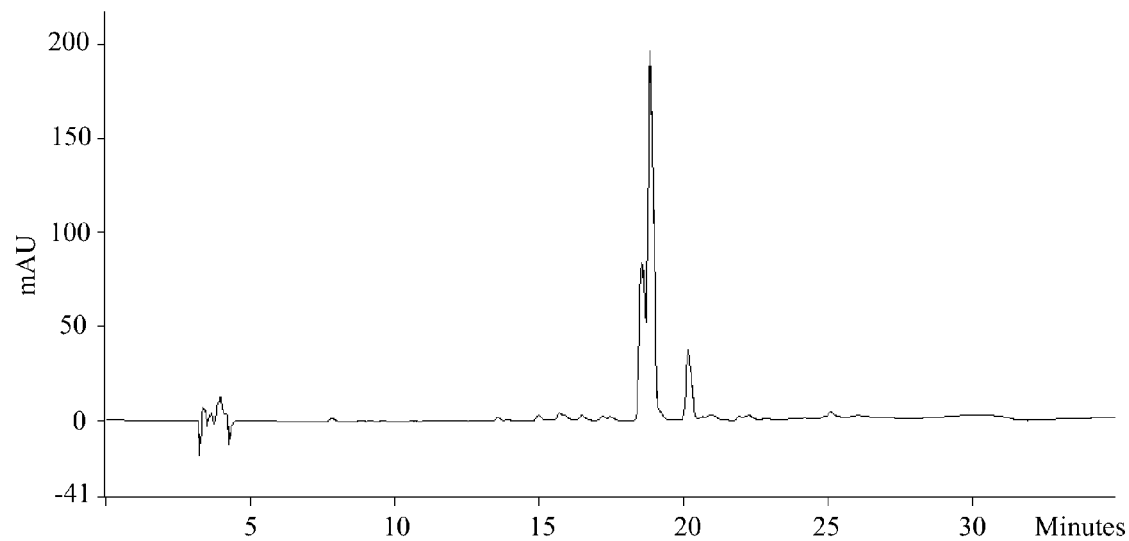
Figure 22:
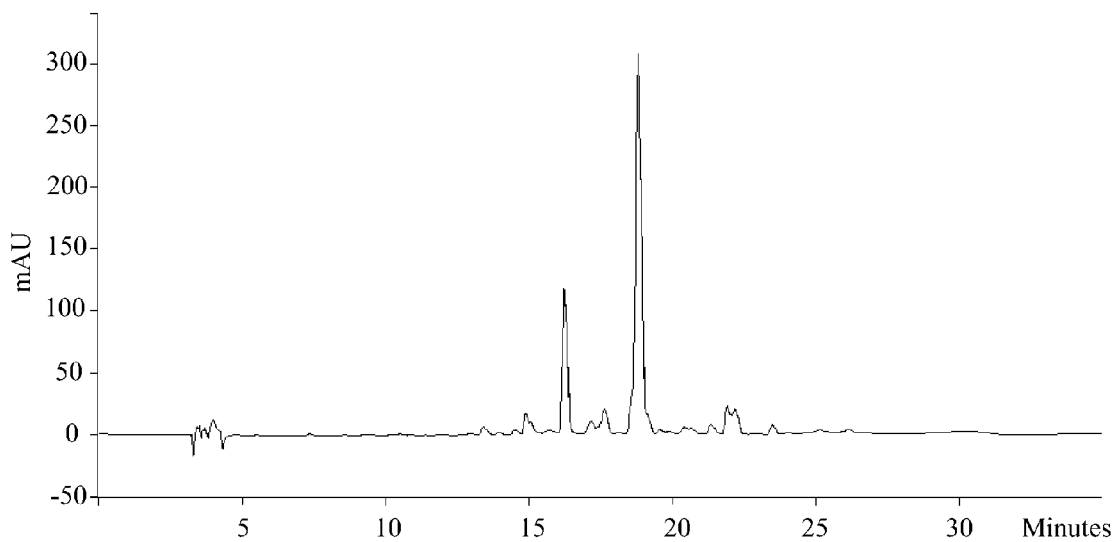
FIG. 22 shows HPLC traces of purified warfarin neoglycosides having the general structure shown in FIG. 2, run on a Phenomenex Gemini 5 μm C18 110 Å reversed-phase column.
Figure 22:
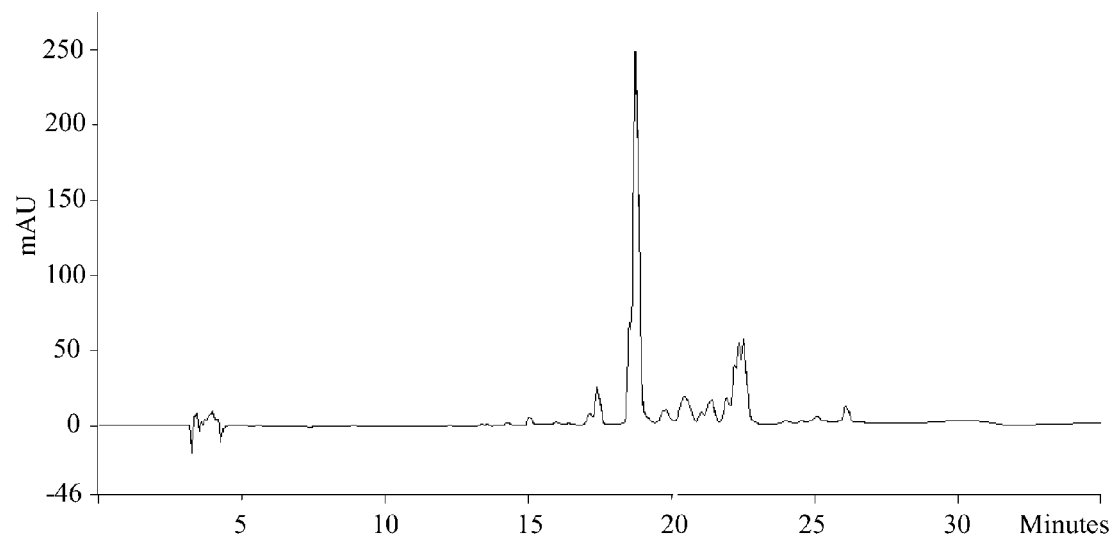
Figure 23:
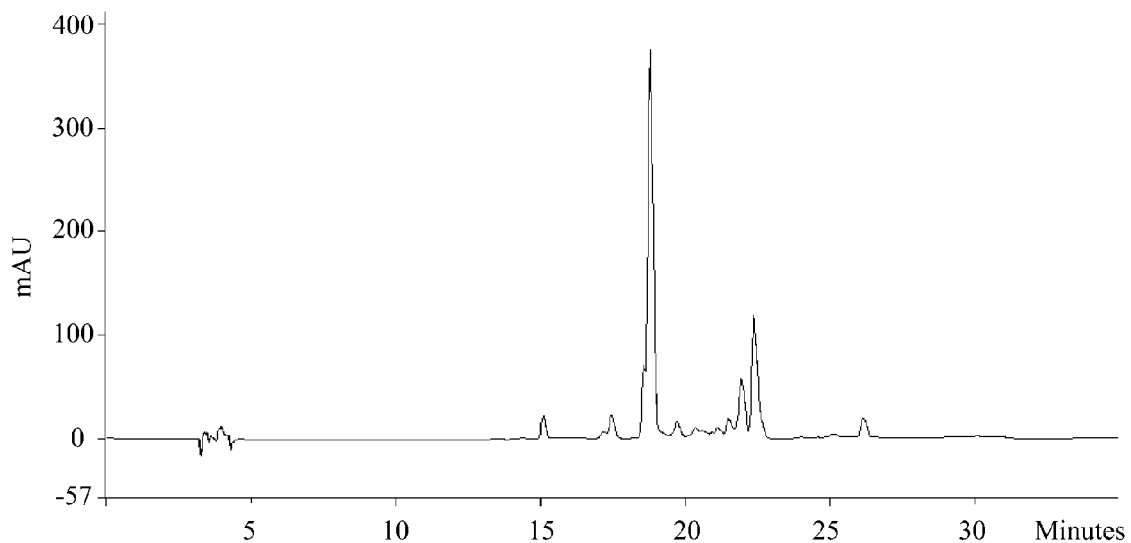
FIG. 23 shows HPLC traces of purified warfarin neoglycosides having the general structure shown in FIG. 2, run on a Phenomenex Gemini 5 μm C18 110 Å reversed-phase column.
Figure 23:
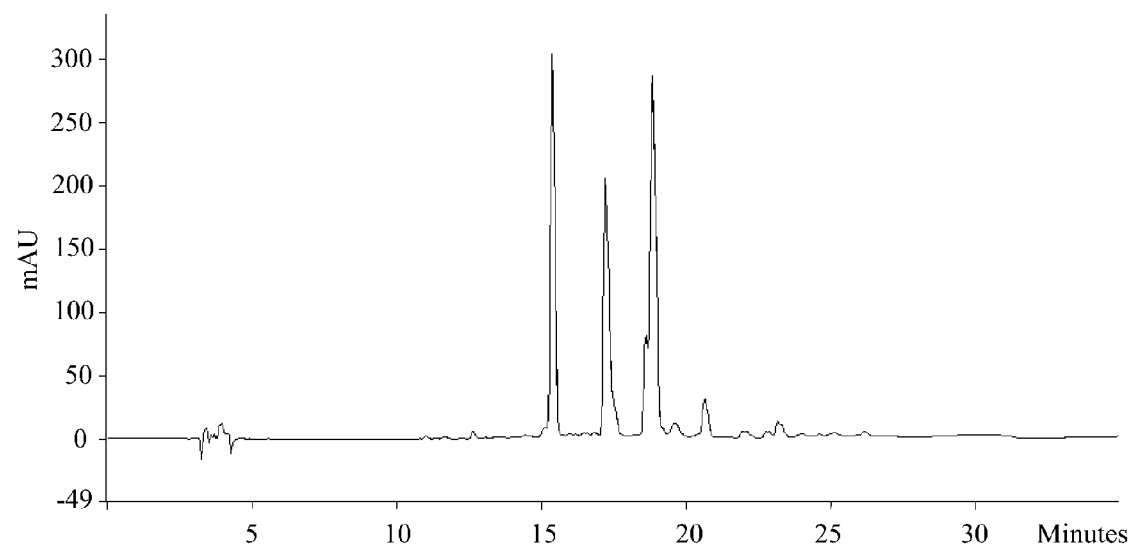
Figure 24:
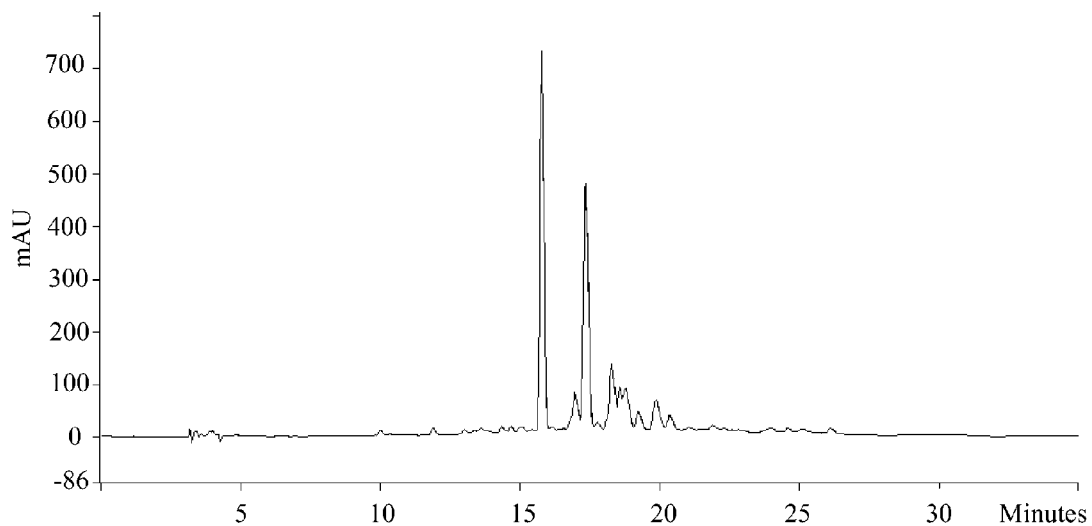
FIG. 24 shows HPLC traces of purified warfarin neoglycosides having the general structure shown in FIG. 2, run on a Phenomenex Gemini 5 μm C18 110 Å reversed-phase column.
Figure 24:
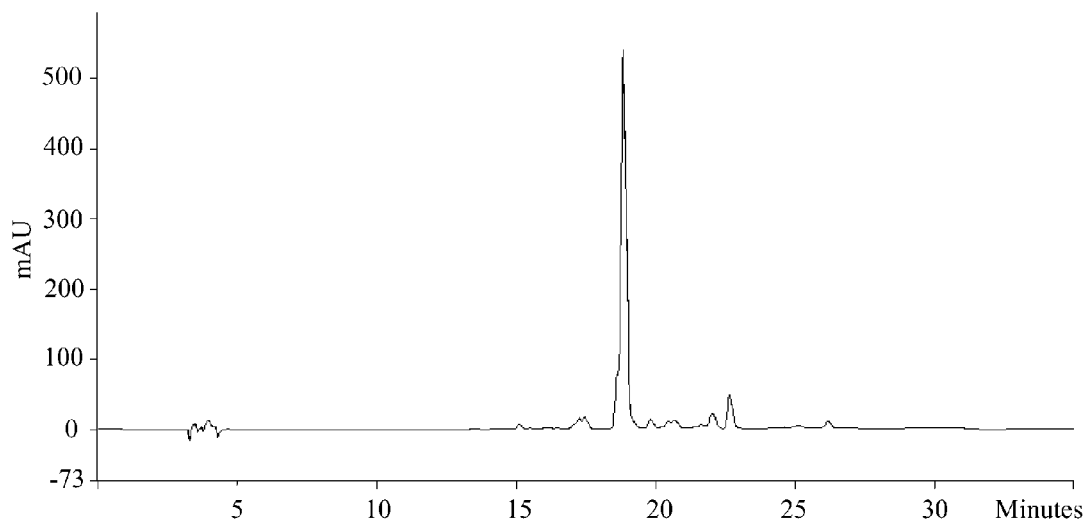
Figure 25:
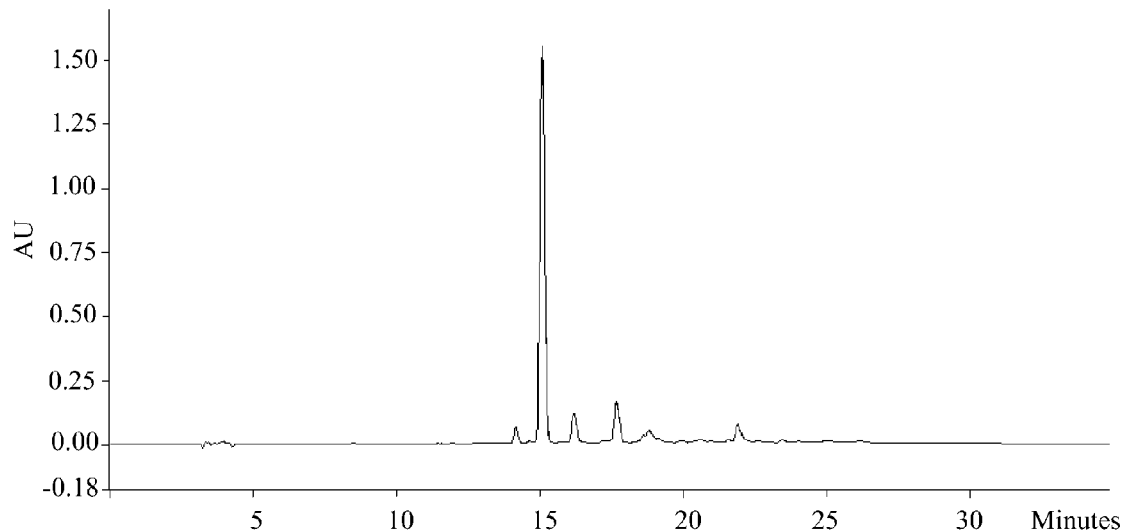
FIG. 25 shows HPLC traces of purified warfarin neoglycosides having the general structure shown in FIG. 2, run on a Phenomenex Gemini 5 μm C18 110 Å reversed-phase column.
Figure 25:
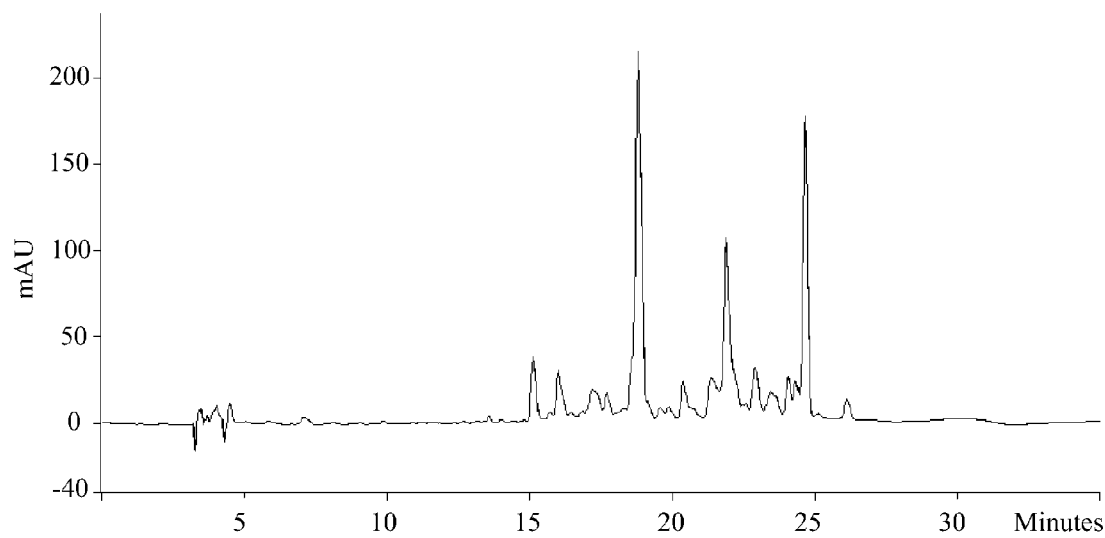
Figure 26:
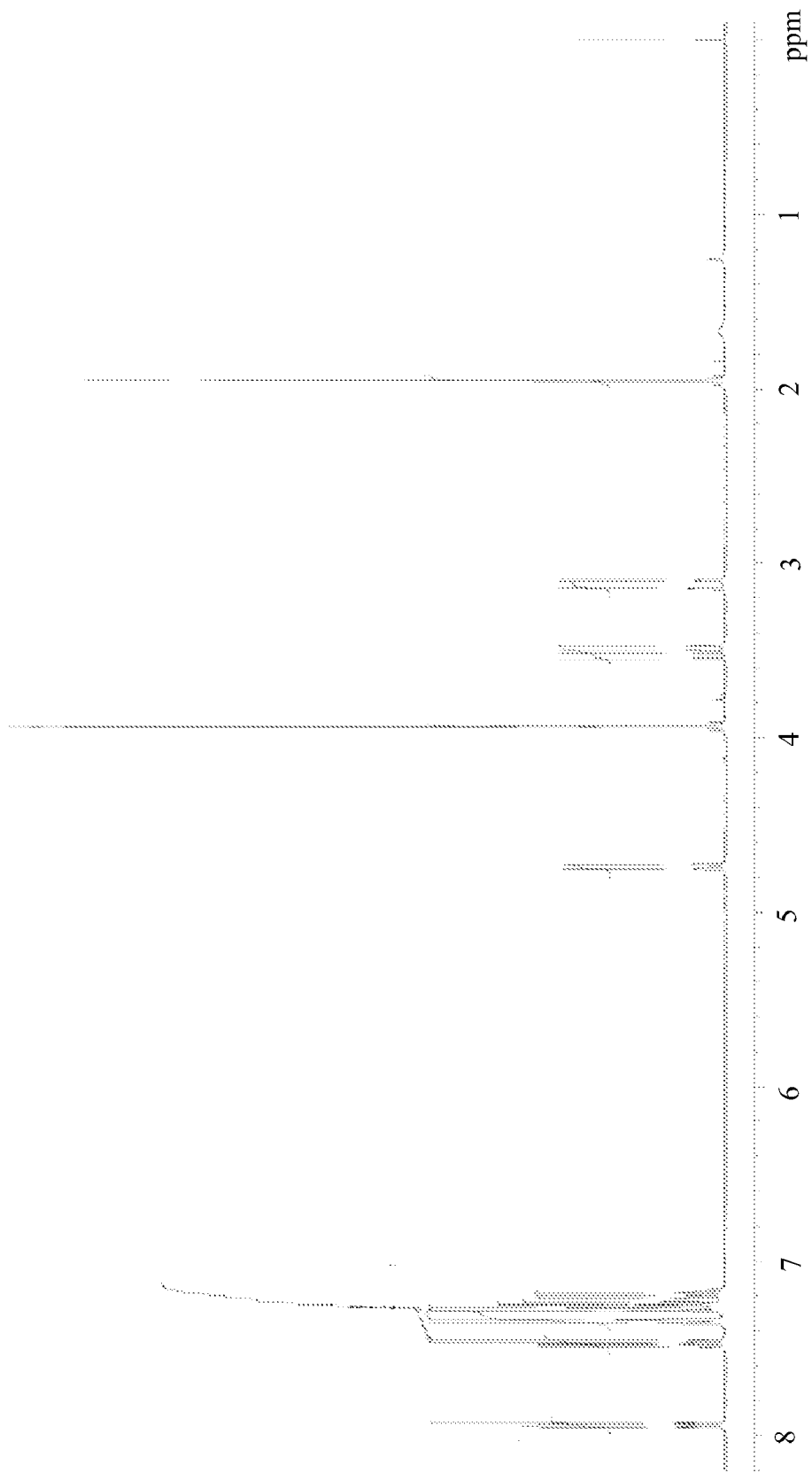
FIG. 26 is a $^1$H nuclear magnetic resonance (NMR) spectrum (400 MHz, CDCl$_3$) for a purified sample of the warfarin analog oxime having the structure shown in FIG. 5.
Figure 27:
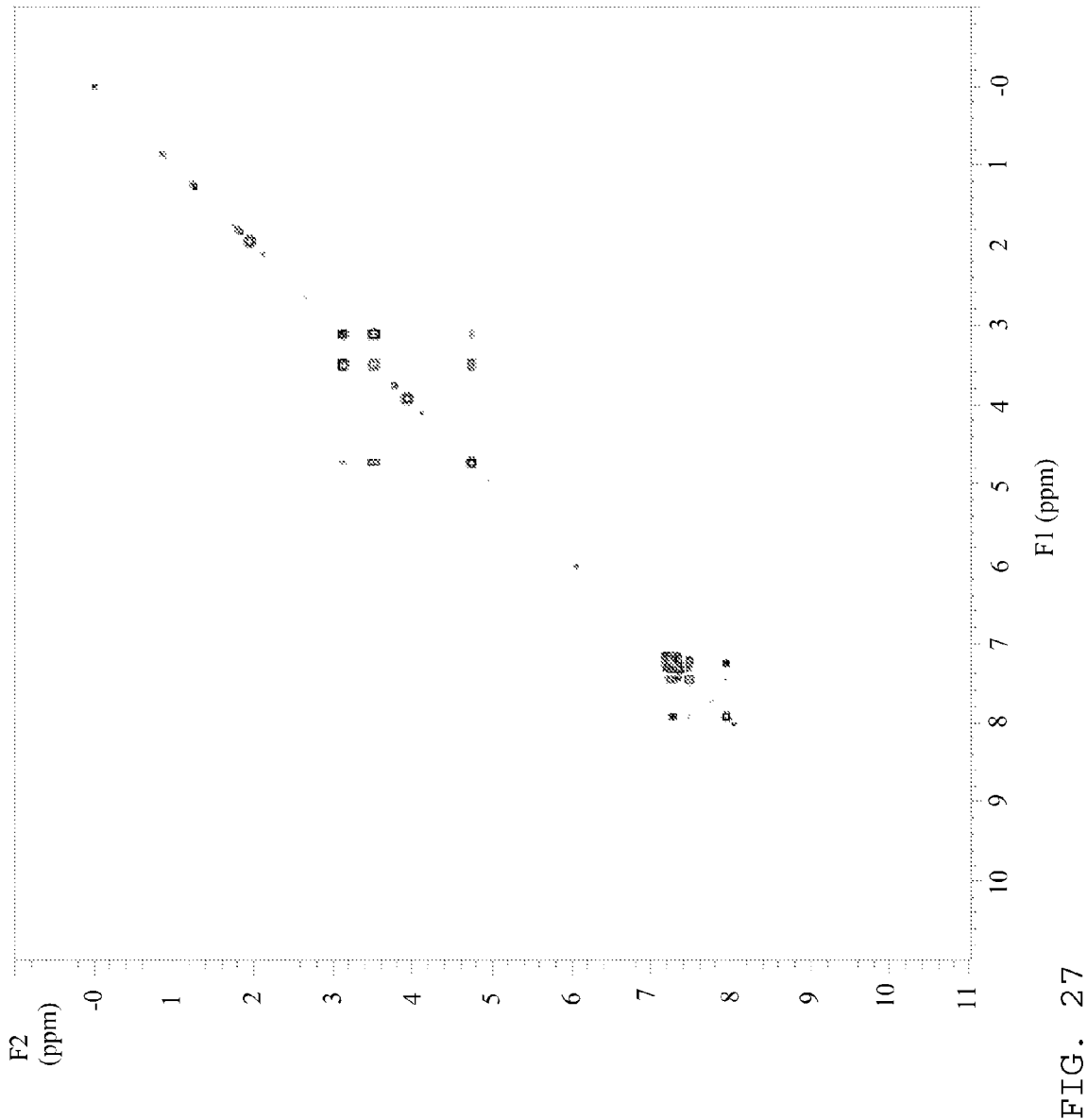
FIG. 27 is a correlation spectroscopy nuclear magnetic resonance (COSY NMR) spectrum (400 MHz, CDCl$_3$) for a purified sample of the warfarin analog oxime having the structure shown in FIG. 5.
Figure 28:
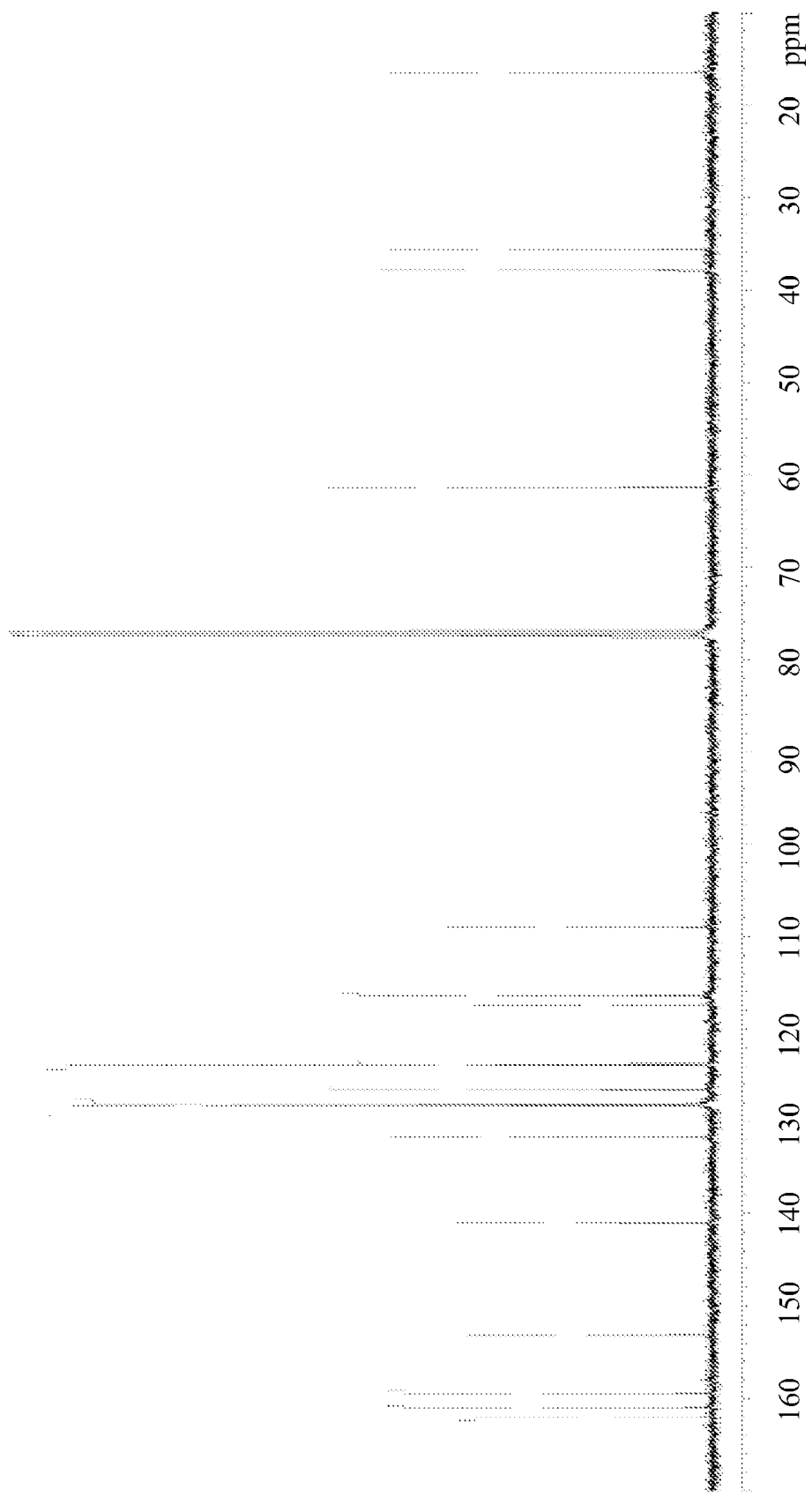
FIG. 28 is a $^{13}$C NMR spectrum (100 MHz, CDCl$_3$) for a purified sample of the warfarin analog oxime having the structure shown in FIG. 5.

The HPLC trace for the warfarin analog oxime product is shown in FIG. 6A. The $^1H$ NMR spectrum of the product is shown in FIG. 26. The COSY NMR spectrum of the product is shown in FIG. 27. The $^{13}C$ NMR spectrum of the product is shown in FIG. 28.

Figure 4:
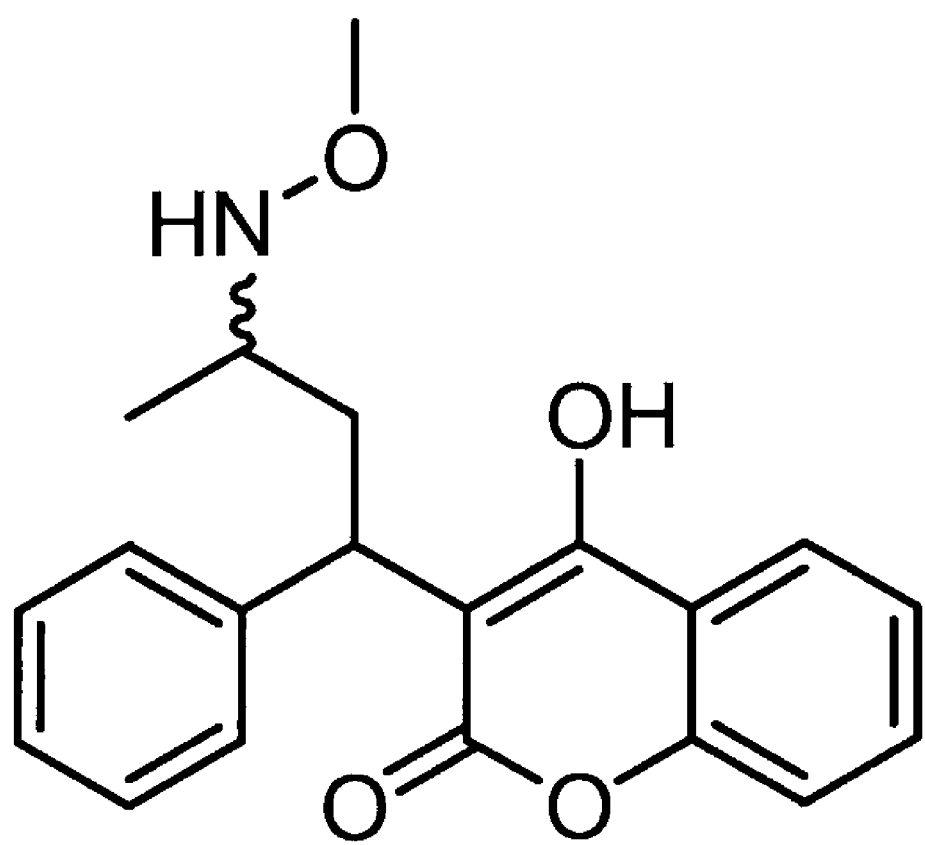
FIG. 4 shows the chemical structure of the warfarin analog aglycon 4-hydroxy-3-(3-(methoxyamino)-1-phenylbutyl)-2H-1-benzopyran-2-one, which is the second intermediate of the general synthesis strategy used to synthesize the warfarin neoglycosides of the present invention. This warfarin analog aglycon is reacted with varying reducing sugars in the third step of the general synthesis strategy to produce the warfarin neoglycosides of the present invention.

Preparation and characterization of 4-hydroxy-3-(3-(methoxyamino)-1-phenylbutyl)-2H-1-benzopyran-2-one (warfarin analog aglycon; FIG. 4). The Warfarin analog oxime (FIG. 5) synthesized in previous step (5.43 g, 16.1 mmol) was dissolved in a mixture of absolute ethanol (23 mL) and 1,4-dioxane (65 mL) in a round-bottomed flask, which was subsequently cooled to 0-5° C. in an ice-water bath. Following the addition of 2 equivalents borane tert-butylamine complex (2.80 g, 32.2 mmol), 10% aq HCl (27 mL) was added dropwise and the reaction mixture was stirred at 0-5° C. for 1 h. After 1, 2, 3, and 4 h time intervals, additional borane tert-butylamine complex (2.80 g, 32.2 mmol) and 10% aq HCl (27 mL) were added.

Following reaction completion (5 h), solid $Na_2CO_3$ was added in small portions until gas evolution ceased and the reaction mixture was partitioned between saturated aq $NaHCO_3$ (500 mL) and $CH_2Cl_2$ (500 mL). The organic layer was washed with saturated aq $NaHCO_3$ (250 mL), dried over $Na_2SO_4$, filtered, and concentrated under reduced pressure to afford a white solid (4.71 g, 13.9 mmol, 86% yield). This product (TLC $R_f$=0.26 in 1:1 EtOAc/hexanes) was used without further purification.

The following is the melting point and spectral data for the resulting product: mp 113-118° C. (mixture of diastereomers); $^1H$ NMR (400 MHz, DMSO-$d_6$): 7.94 (dd, J=1.6, 7.6 Hz, 1H, Ph), 7.47 (m, 1H, Ph), 7.34 (m, 2H, Ph), 7.26-7.05 (m, 5H, Ph), 5.07 (br s, 1H, NH), 4.50 (dd, J=5.8, 10.6 Hz, 1H, CH(Ph)), 3.56 (s, 3H, diastereomeric $OCH_3$), 3.48 (s, 3H, diastereomeric $OCH_3$), 2.89 (m, 1H, $CH(CH_3)$), 2.21 (m, 2H, $CH_2$), 1.24 (s, 3H, diastereomeric $CH(CH_3)$), 1.10 (s, 3H, diastereomeric $CH(CH_3)$) (Note that three other minor $CH(CH_3)$ resonances were observable at 1.20, 1.08, and 1.06 ppm, which were attributed to alternative conformations (e.g., hydrogen bonding, aggregation, etc. . . . ). These peaks became broader over time and their ratio was also affected. This conformational variability also occurred at a slower rate in $CDCl_3$); $^{13}C$ NMR (100 MHz, DMSO-$d_6$): δ 166.3, 162.0, 152.8, 144.6, 130.6, 128.3, 127.7, 127.5, 127.2, 125.2, 124.0, 122.7, 119.3, 116.9, 115.6, 103.8, 66.3, 61.2, 53.6, 52.8, 51.0, 50.6, 36.1, 34.6, 27.2, 27.1, 18.4; HRMS-ESI (m/z): [M-H]⁻ calcd for $C_{20}H_{20}NO_4$, 338.1397; found, 338.1384.

Figure 29:
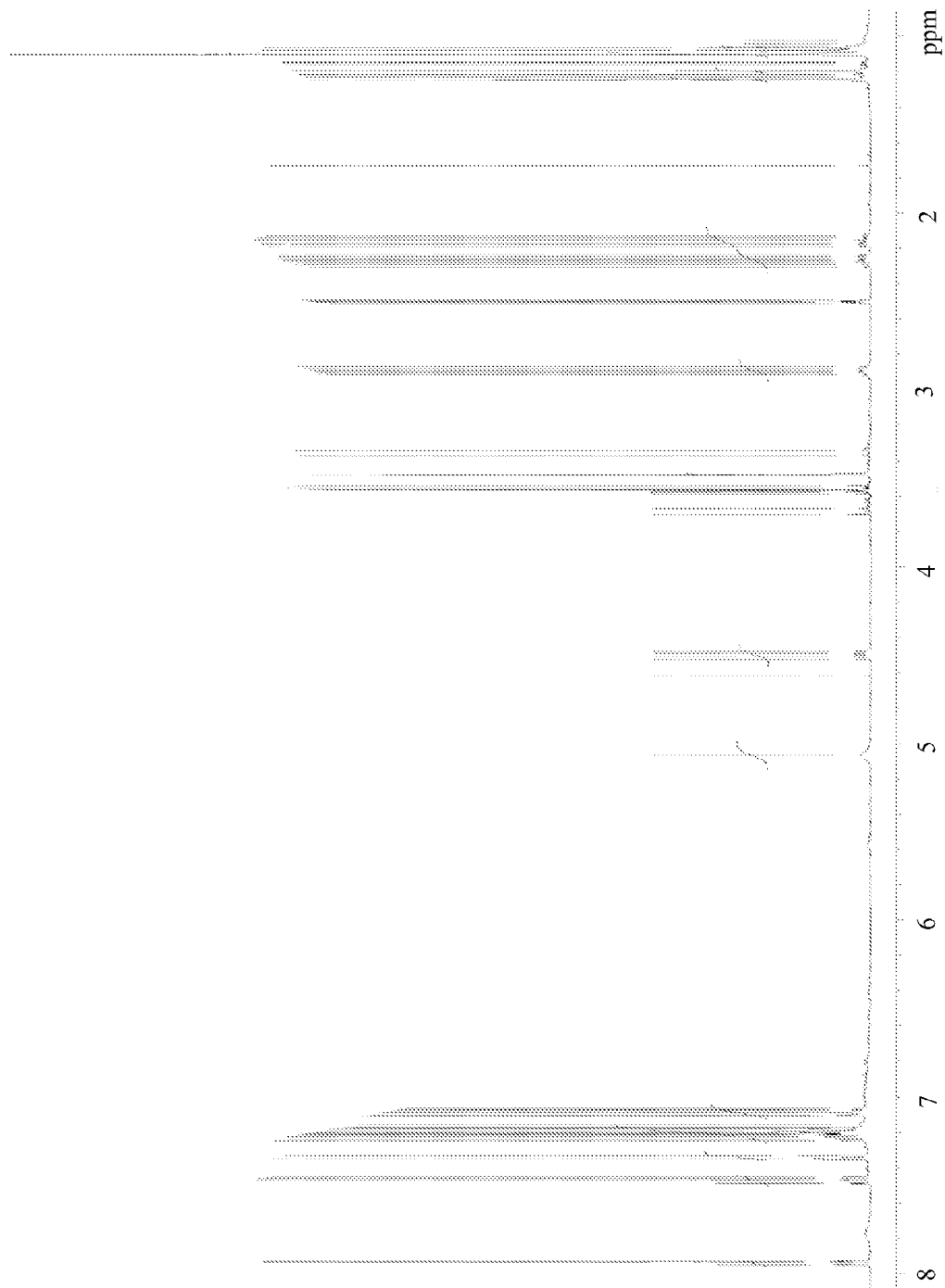
FIG. 29 is a $^1$H NMR spectrum (400 MHz, CDCl$_3$) for a purified sample of the warfarin analog aglycon having the structure shown in FIG. 4.
Figure 30:
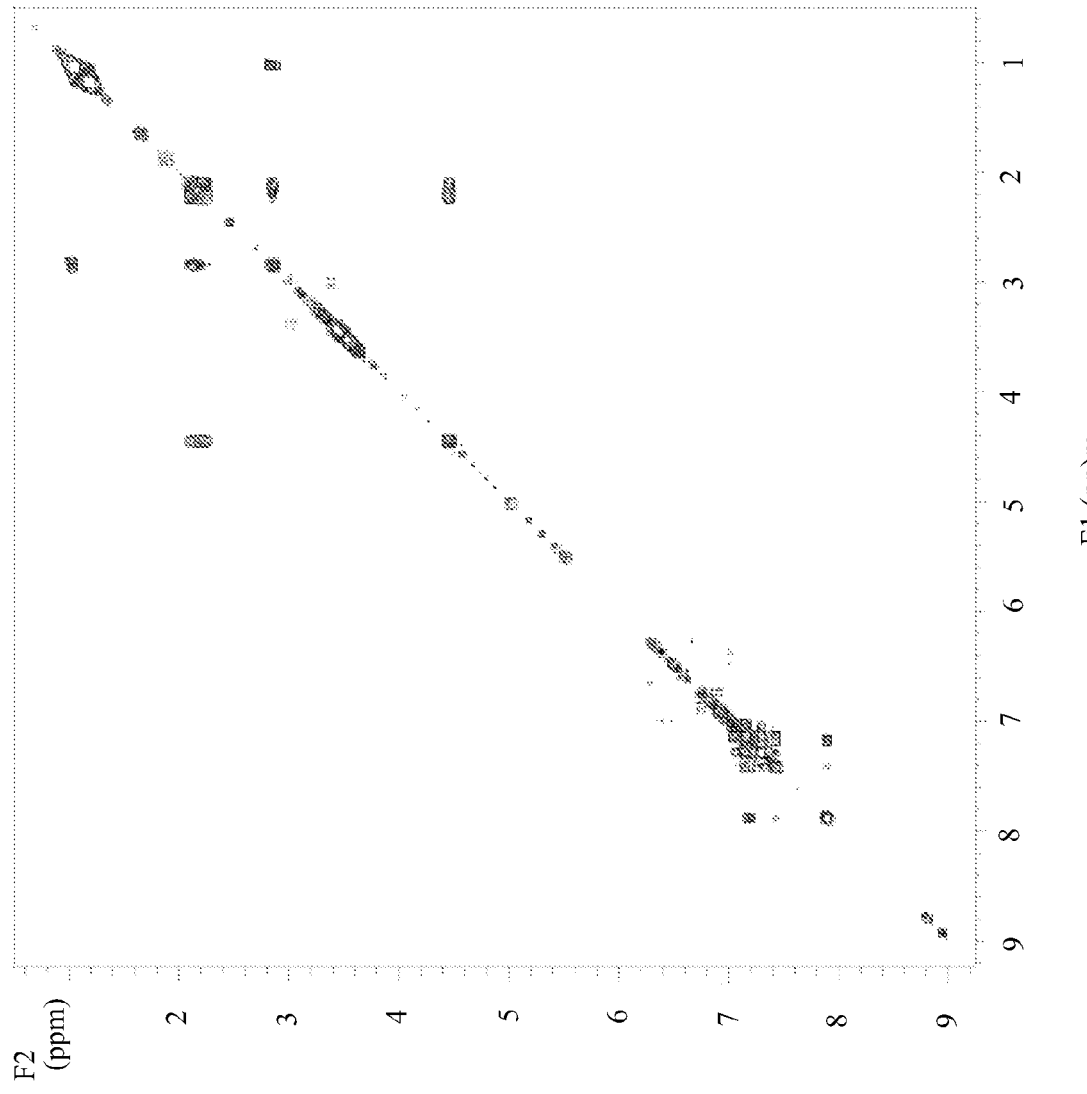
FIG. 30 is a COSY NMR spectrum (400 MHz, CDCl$_3$) for a purified sample of the warfarin analog aglycon having the structure shown in FIG. 4.
Figure 31:
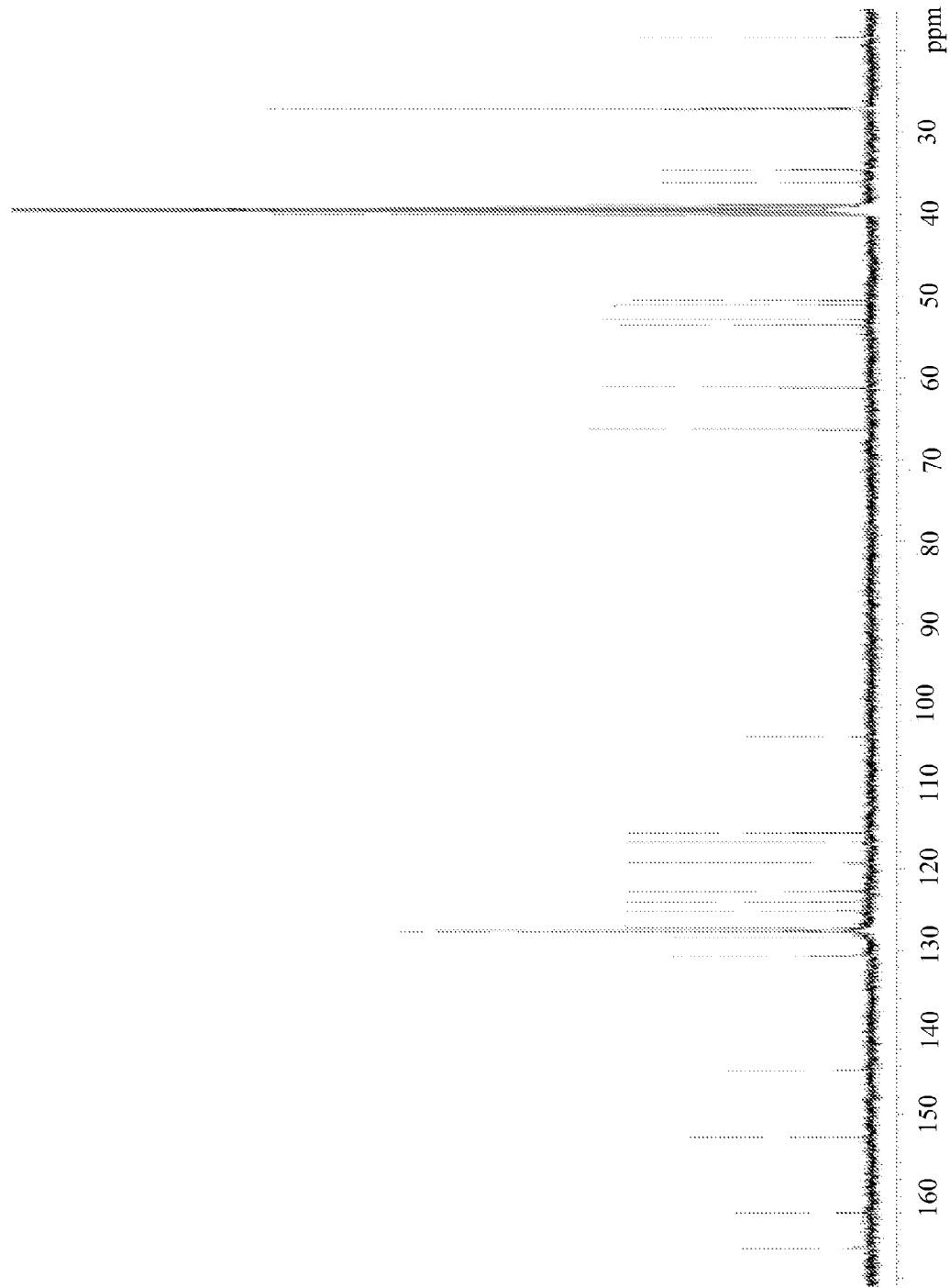
FIG. 31 is a $^{13}$C NMR spectrum (100 MHz, CDCl$_3$) for a purified sample of the warfarin analog aglycon having the structure shown in FIG. 4.

The HPLC trace for the warfarin analog aglycon product is shown in FIG. 6B. The $^1H$ NMR spectrum of the product is shown in FIG. 29. The COSY NMR spectrum of the product is shown in FIG. 30. The $^{13}C$ NMR spectrum of the product is shown in FIG. 31.

General procedure for the preparation of warfarin neoglycosides. Warfarin neoglycosides were synthesized using the following sugars: L-xylose; D-galactosamine; 2-deoxy-D-galactose; L-rhamnose; D-glucuronic acid; D-lyxose; L-glucose; 2-deoxy-D-glucose; D-xylose; 2-deoxy-L-ribose; 2-deoxy-D-ribose; L-fucose; 2,3,4-tri-O-acetyl-L-rhamnose; D-glucose; L-arabinose; D-mannose; D-galactose; 3-O-methyl-D-glucose; L-mannose; N-acetyl-D-mannosamine; D-arabinose; D-ribose; L-lyxose; N-acetyl-D-galactosamine; L-ribose; D-cellobiose; D-galacturonic acid; D-maltose; D-melibiose; N-acetyl-D-glucosamine; 2,3,4,6-tetra-O-acetyl-D-glucose; maltotriose; D-glucuronic acid lactone; α-lactose; L-sorbose; L-noviose; L-mycarose; D-talose; D-allose; D-fucose; 2,3,4,6-tetra-O-benzyl-D-glucose; 2,3,5-tri-O-benzyl-D-arabinofuranose; N-acetylmuramic acid, D-glucosamine; 2,3,4,6-tetra-O-benzyl-D-mannose; 2,3,5-tri-O-benzyl-D-ribofuranose; L-erythrose; L-gulose; D-digitoxose; 6-deoxy-D-glucose; and 2-deoxy-2-fluoro-D-glucose. For each neoglycoside, the warfarin aglycon (FIG. 4; 100 mg, 0.30 mmol) and the selected sugar (0.60 mmol) were suspended in 3:1 DMF/glacial acetic acid (2 mL) in a 1 dram vial.

The reaction mixture was stirred at 50° C. for 24 or 48 h. Following concentration under reduced pressure, the resulting residue was re-suspended in $CH_2Cl_2$ (2 mL) and mixed thoroughly using a vortex mixer. The resulting mixture was centrifuged at 800 rpm for 30 min-1 h to pellet unreacted sugar, which was discarded. Warfarin neoglycosides (contained in the supernatant) were purified using an Isco CombiFlash® Sg 100c Separation System as described in the General Methods section above. The purified warfarin neoglycosides were then characterized by LC-MS and HRMS.

Characterization of the warfarin neoglycosides. 38 of the 51 purified warfarin neoglycosides had sufficient product to accurately characterize. The HPLC traces for these 38 of the warfarin neoglycosides are shown in FIGS. 7-25. Additional data characterizing these warfarin neoglycosides is summarized in Table 1.

TABLE 1

Characterization of Warfarin Neoglycoside Library

| WARF Analog | Sugar | Rxn Time (h) | Purification Method | Appearance | Yield (%) | Calculated Mass [M − H]⁻ | Observed Mass [M + H]⁺ | Purity by LC-MS (%) |
|---|---|---|---|---|---|---|---|---|
| 1 | L-xylose | 48 | A | orange syrup | 45 | 470.1820 | 470.1837 | 98 |
| 2 | L-galactosamine | 48 | n/a | no product | n/a | n/a | n/a | n/a |
| 3 | 2-deoxy-D-galactose | 48 | A | orange solid | 53 | 486.2133 | 486.2127 | 94 |
| 4 | L-rhamnose | 48 | A | pale yellow solid | 38 | 484.1976 | 484.1959 | 97 |
| 5 | D-glucuronic acid | 48 | A | yellow syrup | 15 | 514.1718 | 514.1706 | 98 |
| 6 | D-lyxose | 48 | A | orange syrup | 47 | 470.1820 | 470.1828 | 97 |
| 7 | L-glucose | 48 | A | yellow syrup | 35 | 500.1926 | 500.1909 | 90 |
| 8 | 2-deoxy-D-glucose | 24 | A | orange syrup | 45 | 486.2133 | 486.2154 | 87 |
| 9 | D-xylose | 48 | A | orange syrup | 32 | 470.1820 | 470.1817 | 95 |
| 10 | 2-deoxy-L-ribose | 24 | A | orange syrup | 53 | 456.2077 | 456.2016 | 82 |
| 11 | 2-deoxy-D-ribose | 24 | A | orange syrup | 51 | 456.2027 | 456.2039 | 87 |
| 12 | L-fucose | 48 | A | yellow syrup | 70 | 484.1978 | 484.1957 | 93 |
| 13 | 2,3,4-tri-O-acetyl-D-rhamnose | 24 | n/a | no product | n/a | n/a | n/a | n/a |
| 14 | D-glucose | 48 | A | yellow syrup | 37 | 500.1926 | 500.1925 | 92 |
| 15 | L-arabinose | 24 | A | yellow syrup | 61 | 470.1820 | 470.1829 | 88 |
| 16 | D-mannose | 48 | A | orange syrup | 40 | 500.1926 | 500.1923 | 97 |
| 17 | D-galactose | 48 | A | pale yellow solid | 49 | 500.1926 | 500.1906 | 96 |
| 18 | 3-O-methyl-D-glucose | 48 | A | orange syrup | 47 | 514.2082 | 514.2095 | 97 |
| 19 | L-mannose | 48 | A | yellow syrup | 38 | 500.1926 | 500.1928 | 95 |
| 20 | N-acetyl-D-mannosamine[#] | 48 | A | pale yellow solid | 53 | 523.2085 | 523.2083 | 85 |
| 21 | D-arabinose | 24 | A | yellow syrup | 64 | 470.1820 | 470.1805 | 90 |
| 22 | D-ribose | 48 | A | orange syrup | 56 | 470.1820 | 470.1808 | 94 |
| 23 | L-lyxose | 48 | A | orange syrup | 59 | 470.1820 | 470.1804 | 93 |
| 24 | N-acetyl-D-galactosamine[#] | 48 | A | pale yellow solid | 27 | 523.2085 | 523.2081 | 88 |
| 25 | L-ribose | 48 | A | orange syrup | 51 | 470.1820 | 470.1800 | 94 |
| 26 | D-cellobiose | 24 | n/a | no product | n/a | n/a | n/a | n/a |
| 27 | D-galacturonic acid | 48 | A | pale yellow syrup | 28 | 514.1718 | 514.1711 | 86 |
| 28 | D-maltose | 24 | B | white solid | 4 | 662.2454 | 662.2450 | 98 |
| 29 | D-melibiose | 24 | B | pale yellow solid | 7 | 662.2454 | 662.2478 | 90 |
| 30 | N-acetyl-D-glucosamine[#] | 48 | A | orange syrup | 64 | 523.2085 | 523.2081 | 83 |
| 31 | 2,3,4,6-tetra-O-acetyl-n-glucose | 45 | n/a | no product | n/a | n/a | n/a | n/a |
| 32 | maltotriose | 48 | B | colorless syrup | 2 | 824.2982 | 824.2947 | 95 |
| 33 | D-glucuronic acid lactone | 48 | A | orange solid | 36 | 498.1769 | 498.1748 | 91 |
| 34 | H-lactose | 48 | n/a | no product | n/a | n/a | n/a | n/a |
| 35 | L-sorbose | 48 | n/a | no product | n/a | n/a | n/a | n/a |
| 36 | L-noviose* | 48 | A | white solid | 52 | 514.2448 | 514.2444 | 95 |
| 37 | L-mycarose* | 24 | A | yellow syrup | 65 | 484.2184 | 484.2179 | 97 |
| 38 | D-talose | 48 | A | yellow syrup | 20 | 500.1926 | 500.1914 | 92 |
| 39 | D-allose | 48 | A | white solid | 20 | 500.1926 | 500.1915 | 92 |
| 40 | D-fucose | 48 | A | | | | | 96 |
| 41 | 2,3,4,6-tetra-O-benzyl-D-glucose | 24 | n/a | no product | n/a | n/a | n/a | n/a |
| 42 | 2,3,5-tri-O-benzyl-D-arabinofuranose | 24 | n/a | no product | n/a | n/a | n/a | n/a |
| 43 | N-acetylmuramic acid | 24 | n/a | no product | n/a | n/a | n/a | n/a |
| 44 | D-glucosamine | 48 | n/a | no product | n/a | n/a | n/a | n/a |
| 45 | 2,3,4,6-tetra-O-benzyl-D-nannose | 24 | n/a | no product | n/a | n/a | n/a | n/a |
| 46 | 2,3,5-tri-O-benzyl-D-ribofuranose | 24 | n/a | no product | n/a | n/a | n/a | n/a |
| 47 | L-erythrose | 48 | A | yellow syrup | 14 | 442.1871 | 442.1866 | 93 |
| 48 | L-gulose | 48 | A | yellow solid | 34 | 500.1926 | 500.1919 | 92 |
| 49 | D-digitoxose | 24 | A | orange solid | 65 | 470.2184 | 470.2166 | 90 |
| 50 | 6-deoxy-D-glucose | 48 | A | orange syrup | 66 | 484.1978 | 484.1971 | 95 |
| 51 | 2-deoxy-2-fluoro-n-glucose | 48 | n/a | no product | n/a | n/a | n/a | n/a |

[#]These neoglycosides were prone to dehydration during mass spectrometry and are reported as [M—H$_2$O—H]⁻.
*Reactions were 1:2 reoaglycon/sugar except for those marked with an asterick in which a 1:1 neoaglycon/sugar ratio was used due to the expense of the sugar.

Example 2

Cell Proliferation Activity of Warfarin Neoglycosides

In this Example, the warfarin neoglycosides of the invention were screened for anti-tumor activity in cell proliferation assays using the following tumor cells lines: A549—human lung adenocarcinoma; H1299—human lung adenocarcinoma (p53 null); HCT-15—human colorectal adenocarcinoma; HT-29—human colorectal adenocarcinoma; MCF7—human breast adenocarcinoma; NCI-H460—human lung adenocarcinoma; SF-268—human CNS adenocarcinoma; and SKOV-3—human ovarian adenocarcinoma. A number of the neoglycosides exhibited significant activity against one or more of the tumor cell lines, with such activity being substantially greater the activity of warfarin or the warfarin analog aglycon used in the synthesis of the neoglycosides. This data indicates that some of the neoglycosides may useful as anti-tumor compounds.

General Methods

All cell lines were maintained as previously reported (see Langenhan, J. M.; Peters, N. R.; Guzei, I. A.; Hoffmann, F. M.; Thorson, J. S. Proc. Natl. Acad. Sci. USA 2005, 102, 12305-12310, which is incorporated by reference herein). Cells were harvested using 0.25% trypsin and 0.1% EDTA and counted in a Cellometer Auto T4 cell counter (Nexcelom, Inc.) prior to dilution for assay plating. Cells were plated at a denity of 500 cells per well in 50 µL volumes in 384-well clear-bottom tissue culture plates (Corning-Costar, Inc.).

Compounds were added from the 384-well compound stock plates at a 1:100 dilution using a Biomek FX liquid handler equipped with a 384-channel head (Beckman Coulter, Inc.). The plates were incubated for 7 days at 37° C. in a 5% $CO_2$ atmosphere prior to performing the assays. Calcein AM (acetoxymethyl ester) reagent and EthD-1 (30 µL, 10 µM CAM and 100 µM EthD-1) was added and the cells were incubated for 30 min at 37° C. Luminescence resulting from incubation with Calcein AM and EthD-1 was read using a Safire-2 microplate reader at the appropriate wavelengths. To lyse the cells, 15 µL of CellTiter-Glo reagent (Promega Corporation, Inc.) was added and the cells were incubated for 10 min at room temperature with gentle agitation. The luminescence of each plate was re-read to confirm the observed inhibition.

$IC_{50}$s for cell proliferation assays were determined for Calcein AM, the ratio of live/dead cells (Calcein AM/EthD-1), and CellTiter-Glo using XLfit 4.0 as previously described (see Langenhan, J. M.; Peters, N. R.; Guzei, I. A.; Hoffmann, F. M.; Thorson, J. S. Proc. Natl. Acad. Sci. USA 2005, 102, 12305-12310, which is incorporated by reference herein). The $IC_{50}$ determined using the best fit curve for dosage response from any of the 3 assays is reported as the final $IC_{50}$. The best fit curve is defined as the curve with the lowest standard error.

Results

Table 2 summarizes the results of the cell proliferation assays. Note that a number of the warfarin neoglycans have substantially greater anti-tumor activity than warfarin, warfarin oxime, or warfarin neoglycan. Note also that in most cases, anti-tumor activity shows significant cell type specificity.

TABLE 2

Warfarin neoglycoside cell proliferation activity summary*

| WARF Analog | Sugar | A549 $IC_{50}$ (µM) | NCL-H1299 $IC_{50}$ (µM) | HCT-15 $IC_{50}$ (µM) | HT-29 $IC_{50}$ (µM) | MCF-7 $IC_{50}$ (µM) | NCI/ADR-RES $IC_{50}$ (µM) | NCI-H460 $IC_{50}$ (µM) | SF-268 $IC_{50}$ (µM) | SK-OV-3 $IC_{50}$ (µM) |
|---|---|---|---|---|---|---|---|---|---|---|
| A | warfarin | 781 | 380 | 543 | 735 | 301 | >100 | 557 | 765 | 393 |
| B | warfarin oxime | >100 | >100 | 83 | 91 | >100 | >100 | >100 | >100 | >100 |
| C | warfarin neoaglycon | >100 | >100 | >100 | >100 | >100 | >100 | >100 | >100 | >100 |
| 1 | L-xylose | 67 | 30 | 14 | 37 | 15 | 50 | >100 | 39 | 45 |
| 3 | 2-deoxy-D-galactose | >100 | >100 | >100 | >100 | >100 | >100 | >100 | >100 | >100 |
| 4 | L-rhamnose | >100 | 78 | >100 | >100 | >100 | 92 | >100 | >100 | >100 |
| 5 | D-glucuronic acid | >100 | >100 | >100 | >100 | >100 | >100 | >100 | >100 | >100 |
| 6 | D-lyxose | 76 | 28 | 7 | 52 | 28 | 57 | >100 | 39 | 47 |
| 7 | L-glucose | >100 | 83 | >100 | >100 | >100 | >100 | >100 | >100 | >100 |
| 8 | 2-deoxy-D-glucose | >100 | >100 | >100 | >100 | >100 | >100 | >100 | >100 | >100 |
| 9 | D-xylose | 40 | 27 | 11 | 43 | 12 | 38 | 99 | 37 | 52 |
| 10 | 2-deoxy-L-ribose | >100 | 77 | 12 | 88 | 66 | 92 | >100 | >100 | >100 |
| 11 | 2-deoxy-D-ribose | >100 | 92 | 13 | >100 | 78 | >100 | >100 | >100 | >100 |
| 12 | L-fucose | >100 | >100 | 9 | 80 | >100 | >100 | >100 | 89 | 81 |
| 13 | 2,3,4-tri-O-Ac-L-rhamnose | >100 | >100 | 38 | >100 | >100 | >100 | >100 | >100 | >100 |
| 14 | D-glucose | >100 | 72 | >100 | >100 | >100 | 94 | >100 | >100 | >100 |
| 15 | L-arabinose | 48 | 51 | 49 | 97 | 79 | 68 | >100 | 69 | 76 |
| 16 | D-mannose | >100 | 90 | 53 | >100 | 93 | >100 | >100 | >100 | >100 |
| 17 | D-galactose | >100 | 57 | >100 | >100 | 52 | >100 | >100 | 62 | >100 |
| 18 | 3-O-methyl-D-glucose | >100 | >100 | >100 | >100 | >100 | >100 | >100 | >100 | >100 |
| 19 | L-mannose | >100 | >100 | 80 | 99 | >100 | >100 | >100 | >100 | >100 |
| 20 | N-acetyl-D-mannosamine | >100 | >100 | >100 | >100 | >100 | >100 | >100 | >100 | >100 |
| 21 | D-arabinose | >100 | >100 | >100 | >100 | 90 | >100 | >100 | >100 | >100 |
| 22 | D-ribose | >100 | 44 | 27 | 77 | 41 | 66 | >100 | 72 | 60 |
| 23 | L-lyxose | 95 | 30 | 14 | 47 | 18 | 56 | >100 | >100 | 60 |
| 24 | N-acetyl-D-galactosamine | >100 | >100 | >100 | >100 | >100 | >100 | >100 | >100 | >100 |
| 25 | L-ribose | 72 | 35 | 37 | 72 | 45 | 62 | >100 | >100 | 60 |
| 26 | b-cellobiose | >100 | >100 | >100 | >100 | >100 | >100 | >100 | >100 | >100 |
| 27 | D-galacturonic acid | >100 | >100 | >100 | >100 | >100 | >100 | >100 | >100 | >100 |

TABLE 2-continued

Warfarin neoglycoside cell proliferation activity summary*

| WARF Analog | Sugar | A549 IC$_{50}$ (μM) | NCL-H1299 IC$_{50}$ (μM) | HCT-15 IC$_{50}$ (μM) | HT-29 IC$_{50}$ (μM) | MCF-7 IC$_{50}$ (μM) | NCI/ADR-RES IC$_{50}$ (μM) | NCI-H460 IC$_{50}$ (μM) | SF-268 IC$_{50}$ (μM) | SK-OV-3 IC$_{50}$ (μM) |
|---|---|---|---|---|---|---|---|---|---|---|
| 28 | D-maltose | >100 | >100 | >100 | >100 | >100 | >100 | >100 | >100 | >100 |
| 29 | D-melibiose | >100 | >100 | >100 | 98 | >100 | >100 | >100 | >100 | >100 |
| 30 | N-acetyl-D-glucosamine | >100 | >100 | >100 | >100 | >100 | >100 | >100 | >100 | >100 |
| 31 | 2,3,4,6-tetra-O-Ac-D-glucose | >100 | 50 | 11 | 39 | 16 | 72 | >100 | 50 | >100 |
| 32 | maltotriose | >100 | >100 | >100 | >100 | >100 | >100 | >100 | >100 | >100 |
| 33 | D-glucuronic acid lactone | >100 | >100 | >100 | >100 | >100 | >100 | >100 | >100 | >100 |
| 35 | L-sorbose | >100 | >100 | 58 | >100 | >100 | >100 | >100 | >100 | >100 |
| 36 | L-noviose | >100 | >100 | >100 | >100 | >100 | >100 | >100 | >100 | >100 |
| 37 | L-mycarose | >100 | >100 | 16 | >100 | >100 | >100 | >100 | >100 | >100 |
| 38 | D-talose | >100 | >100 | >100 | >100 | >100 | >100 | >100 | >100 | 61 |
| 39 | D-allose | >100 | >100 | >100 | >100 | >100 | >100 | >100 | >100 | >100 |
| 40 | D-fucose | >100 | >100 | >100 | 89 | >100 | >100 | >100 | >100 | >100 |
| 41 | 2,3,4,6-tetra-O-Bn-D-glucose | 44 | 28 | 22 | 30 | 57 | 35 | 86 | 35 | 30 |
| 42 | 2,3,5-tri-O-Bn-D-arabinofuranose | 27 | 19 | 11 | 19 | 29 | 20 | 46 | 20 | 27 |
| 43 | N-acetylmuramic acid | >100 | >100 | >100 | >100 | >100 | >100 | >100 | >100 | >100 |
| 45 | 2,3,4,6-tetra-O-Bn-D-mannose | 29 | 19 | 13 | 15 | 31 | 26 | 48 | 28 | 18 |
| 46 | 2,3,5-tri-O-Bn-D-ribofuranose | 29 | 19 | 12 | 18 | 27 | 24 | 48 | 20 | 18 |
| 47 | L-erythrose | >100 | >100 | >100 | >100 | 92 | >100 | >100 | >100 | >100 |
| 48 | L-gulose | >100 | >100 | >100 | >100 | >100 | >100 | >100 | >100 | >100 |
| 49 | D-digitoxose | >100 | >100 | >100 | >100 | >100 | >100 | >100 | >100 | >100 |
| 50 | 6-deoxy-D-glucose | >100 | >100 | 14 | >100 | >100 | >100 | >100 | >100 | >100 |
| 51 | 2-deoxy-2-fluoro-D-glucose | >100 | >100 | >100 | >100 | >100 | >100 | >100 | >100 | >100 |

*Standard error (μM) is indicated in parentheses.

Table 3 highlights the anti-tumor activity of the most active of the warfarin neoglycosides. In particular, the data for those warfarin neoglycosides exhibiting high (IC$_{50}$<20) or moderate (IC$_{50}$ 20-100) activity against at least one cell line are shown, along with comparison data for warfarin, warfarin neoaglycon, and the FDG neoglycoside. Thirteen of the warfarin neoglycosides showed high activity against one or more of seven different cell lines. Interestingly, the neoglycoside containing a D-lyxose moiety exhibited the highest level of activity of all the neoglycosides tested, but its activity showed high specificity against a single cell type: HCT 15 colorectal cell lines.

While, the present invention has been described in what is perceived to be the most practical and preferred embodiments and examples, it is to be understood that the invention is not intended to be limited to the specific embodiments set forth above. Rather, it is recognized that modifications may be made by one of skill in the art of the invention without departing from the spirit or intent of the invention and, therefore, the invention is to be taken as including all reasonable equivalents to the subject matter of the appended claims. All references cited herein are incorporated by reference for all purposes.

TABLE 3

Summary of most active compounds as compared to Glc and FDG controls.

| Neoglycoside | A549 Lung (+p53) | H1299 Lung (−p53) | HCT15 Colorectal | H729 Colorectal | MCF7 Breast | NCI/ADR-RES | NCI-H460 Lung | SF268 Giloblast | SKOV3 Ovarian |
|---|---|---|---|---|---|---|---|---|---|
| warfarin | 781 | 380 | 543 | 735 | 301 | >100 | 557 | 765 | 393 |
| warfarin neoaglycon | >100 | >100 | >100 | >100 | >100 | >100 | >100 | >100 | >100 |
| L-xylose | 67 | 30 | 14 | 37 | 15 | 50 | >100 | 39 | 45 |
| D-xylose | 40 | 27 | 11 | 43 | 12 | 38 | 99 | 37 | 52 |
| L-lyxose | 95 | 30 | 14 | 47 | 18 | 56 | >100 | >100 | 60 |
| D-lyxose | 76 | 28 | 7 | 52 | 28 | 57 | >100 | 39 | 47 |
| L-ribose | 72 | 35 | 37 | 72 | 45 | 62 | >100 | >100 | 60 |
| D-ribose | >100 | 44 | 27 | 77 | 41 | 66 | >100 | 72 | 60 |
| 2-deoxy-L-ribose | >100 | 77 | 12 | 88 | 66 | 92 | >100 | >100 | >100 |
| 2-deoxy-D-ribose | >100 | 92 | 13 | >100 | 78 | >100 | >100 | >100 | >100 |
| L-arabinose | 48 | 51 | 49 | 97 | 79 | 68 | >100 | 69 | 76 |
| L-mycarose | >100 | >100 | 16 | >100 | >100 | >100 | >100 | >100 | >100 |
| L-fucose | >100 | >100 | 9 | 80 | >100 | >100 | >100 | 89 | 81 |
| 6-deoxy-D-glucose | >100 | >100 | 14 | >100 | >100 | >100 | >100 | >100 | >100 |
| 2,3,4,6-tetra-O-Ac-D-glucose | >100 | 50 | 11 | 39 | 16 | 72 | >100 | 50 | >100 |
| 2,3,4,6-tetra-O-Bn-D-glucose | 44 | 28 | 22 | 30 | 57 | 35 | 86 | 35 | 30 |
| 2,3,4,6-tetra-O-Bn-D-mannose | 29 | 19 | 13 | 15 | 31 | 26 | 48 | 28 | 18 |
| 2,3,5-tri-O-Bn-D-arabinofuranose | 27 | 19 | 11 | 19 | 29 | 20 | 48 | 20 | 27 |
| 2,3,5-tri-O-Bn-D-ribofuronose | 29 | 19 | 12 | 18 | 27 | 24 | 48 | 20 | 18 |
| 2-deoxy-2-fluoro-D-glucose | >100 | >100 | >100 | >100 | >100 | >100 | >100 | >100 | >100 |

What is claimed is:

1. A composition comprising a warfarin neoglycoside having the general formula:

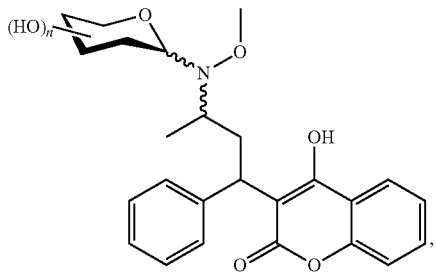

wherein

is a reducing sugar selected from the group consisting of L-xylose; D-lyxose; D-xylose; 2-deoxy-L-ribose; 2-deoxy-D-ribose; L-fucose; L-arabinose; D-ribose; L-lyxose; L-ribose; 2,3,4,6-tetra-O-acetyl-D-glucose; L-mycarose; 2,3,4,6-tetra-O-benzyl-D-glucose; 2,3,5-tri-O-benzyl-D-arabinofuranose; 2,3,4,6-tetra-O-benzyl-D-mannose; 2,3,5-tri-O-benzyl-D-ribofuranose; and 6-deoxy-D-glucose.

2. A composition comprising the warfarin neoglycoside of claim 1 or a pharmaceutically acceptable salt thereof, combined with a pharmaceutically acceptable carrier.

3. A composition comprising a warfarin neoglycoside produced when an aglycon warfarin analog containing a secondary alkoxylamine moiety having the structure:

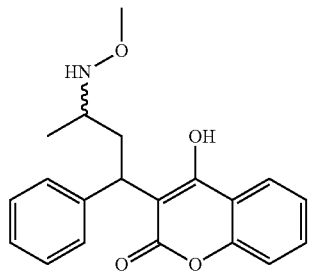

is contacted with a reducing sugar selected from the group consisting of L-xylose; D-lyxose; D-xylose; 2-deoxy-L-ribose; 2-deoxy-D-ribose; L-fucose; L-arabinose; D-ribose; L-lyxose; L-ribose; 2,3,4,6-tetra-O-acetyl-D-glucose; L-mycarose; 2,3,4,6-tetra-O-benzyl-D-glucose; 2,3,5-tri-O-benzyl-D-arabinofuranose; 2,3,4,6-tetra-O-benzyl-D-mannose; 2,3,5-tri-O-benzyl-D-ribofuranose; 6-deoxy-D-glucose; and mixtures thereof.

4. A composition comprising the warfarin neoglycoside of claim 3 or a pharmaceutically acceptable salt thereof, combined with a pharmaceutically acceptable carrier.

5. A method of treating cancer in a subject in need thereof comprising the step of contacting the cancer cells with an effective amount of one or more of a warfarin neoglyoside having the general formula

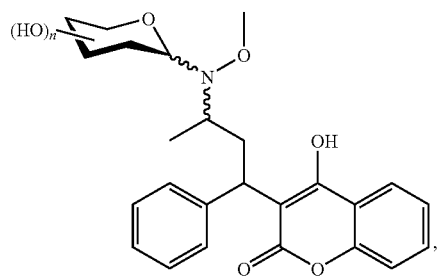

wherein

is a reducing sugar selected from the group consisting of L-xylose; D-lyxose; D-xylose; 2-deoxy-L-ribose; 2-deoxy-D-ribose; L-fucose; L-arabinose; D-ribose; L-lyxose; galactosamine; L-ribose; 2,3,4,6-tetra-O-acetyl-D-glucose; L-mycarose; 2,3,4,6-tetra-O-benzyl-D-glucose; 2,3,5-tri-O-benzyl-D-arabinofuranose; 2,3,4,6-tetra-O-benzyl-D-mannose; 2,3,5-tri-O-benzyl-D-ribofuranose; and 6-deoxy-D-glucose; or a pharmaceutically acceptable salt thereof.

6. The method of claim 5, wherein the cancer cells being contacted with an effective amount of the warfarin neoglycoside or pharmaceutically acceptable salt thereof are selected from human lung adenocarcinoma cells, human colorectal adenocarcinoma cells, human ovarian adenocarcinoma cells, human central nervous system adenocarcinoma cells, and human breast adenocarcinoma cells.

7. The method of claim 6, wherein the cancer cells being contacted are human colorectal adenocarcinoma cells.

8. The method of claim 5, wherein the reducing sugar is selected from the group consisting of L-xylose; D-lyxose; D-xylose; 2-deoxy-L-ribose; 2-deoxy-D-ribose; L-fucose; L-lyxose; 2,3,4,6-tetra-O-acetyl-D-glucose; L-mycarose; 2,3,5-tri-O-benzyl-D-arabinofuranose; 2,3,4,6-tetra-O-benzyl-D-mannose; 2,3,5-tri-O-benzyl-D-ribofuranose; and 6-deoxy-D-glucose.

9. A method of studying sugar uptake in cells comprising the steps of:
(a) contacting cells with a warfarin neoglyoside having the general formula

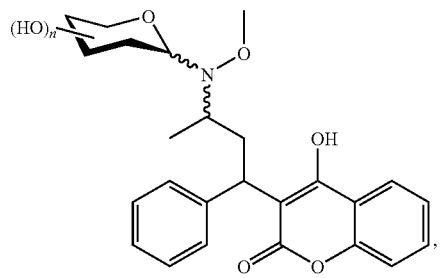

wherein

is a reducing sugar selected from the group consisting of L-xylose; D-lyxose; D-xylose; 2-deoxy-L-ribose; 2-deoxy-D-ribose; L-fucose; L-arabinose; D-ribose; L-lyxose; 2,3,4,6-tetra-O-acetyl-D-glucose; L-mycarose; 2,3,4,6-tetra-O-benzyl-D-glucose; 2,3,5-tri-O-benzyl-D-arabinofuranose; 2,3,4,6-tetra-O-benzyl-D-mannose; 2,3,5-tri-O-benzyl-D-ribofuranose; and 6-deoxy-D-glucose, and (b) measuring the amount of the warfarin neoglycoside taken up by the cells.

10. The method of claim 9, wherein the step of measuring the amount of the warfarin neoglycoside taken up by the cells is performed by a fluorescence-based assay.

\* \* \* \* \*

UNITED STATES PATENT AND TRADEMARK OFFICE
CERTIFICATE OF CORRECTION

| | | |
|---|---|---|
| PATENT NO. | : 8,278,436 B2 | Page 1 of 1 |
| APPLICATION NO. | : 12/512696 | |
| DATED | : October 2, 2012 | |
| INVENTOR(S) | : Jon S. Thorson and Shannon C. Timmons | |

It is certified that error appears in the above-identified patent and that said Letters Patent is hereby corrected as shown below:

Column 13, line 46, "triglyceride" should be --triglycerides--.

Column 25, line 32, "denity" should be --density--.

Column 29, line 66, "neoglyoside" should be --neoglycoside--.

Column 31, line 11, "2,3,4," should be --L-ribose; 2,3,4--.

Signed and Sealed this
First Day of January, 2013

David J. Kappos
*Director of the United States Patent and Trademark Office*